(12) United States Patent
Chavez et al.

(10) Patent No.: US 11,345,931 B2
(45) Date of Patent: May 31, 2022

(54) CAS DISCRIMINATION USING TUNED GUIDE RNA

(71) Applicant: President and Fellows of Harvard College, Cambridge, MA (US)

(72) Inventors: Alejandro Chavez, New York, NY (US); Benjamin W. Pruitt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 502 days.

(21) Appl. No.: 16/061,363

(22) PCT Filed: Dec. 14, 2016

(86) PCT No.: PCT/US2016/066499
§ 371 (c)(1),
(2) Date: Jun. 12, 2018

(87) PCT Pub. No.: WO2017/106251
PCT Pub. Date: Jun. 22, 2017

(65) Prior Publication Data
US 2019/0040416 A1    Feb. 7, 2019

Related U.S. Application Data

(60) Provisional application No. 62/266,851, filed on Dec. 14, 2015.

(51) Int. Cl.
| | | |
|---|---|---|
| C12N 5/00 | (2006.01) | |
| C12N 15/90 | (2006.01) | |
| C12N 15/10 | (2006.01) | |
| A61K 31/713 | (2006.01) | |
| C12N 9/22 | (2006.01) | |
| C12N 15/11 | (2006.01) | |

(52) U.S. Cl.
CPC .......... *C12N 15/902* (2013.01); *A61K 31/713* (2013.01); *C12N 9/22* (2013.01); *C12N 15/102* (2013.01); *C12N 15/1082* (2013.01); *C12N 15/11* (2013.01); *C12N 2310/20* (2017.05); *C12N 2800/80* (2013.01)

(58) Field of Classification Search
CPC ........................ C12N 2800/80; C12N 2310/20; C12N 15/11; C12N 15/1082; C12N 15/102; C12N 9/22; C12N 15/902; A61K 31/713
See application file for complete search history.

(56) References Cited

U.S. PATENT DOCUMENTS

| | | | |
|---|---|---|---|
| 2014/0170753 A1 | 6/2014 | Zhang | |
| 2014/0295556 A1 | 10/2014 | Joung et al. | |
| 2014/0357530 A1* | 12/2014 | Zhang ................ | C12N 15/1034 506/16 |

FOREIGN PATENT DOCUMENTS

| | | | | |
|---|---|---|---|---|
| WO | 2015/123339 A1 | 8/2015 | | |
| WO | WO-2015123339 A1 * | 8/2015 | ............. | C12N 15/11 |

OTHER PUBLICATIONS

Smith et al in "Efficient and Allele-Specific Genome Editing of Disease Loci in Human iPSCs," (Molecular Therapy, Dec. 16, 2014, vol. 23, pp. 570-577; IDS reference). (Year: 2014).*
Liang et al in "Rapid and highly efficient mammalian cell engineering via Cas9 protein transfection," Journal of Biotechnology, May 21, 2015, vol. 208, pp. 44-53; IDS reference). (Year: 2015).*
Sternberg et al "DNA interrogation by the CRISPR RNA-guided endonuclease" (Nature. Mar. 6, 2014: vol. 507, No. 7490: pp. 62-67). (Year: 2014).*
Cong et al. "Multiplex Genome Engineering Using CRISPR/Cas Systems," Science, Feb. 15, 2013 (Feb. 15, 2013), vol. 339, pp. 819-823. entire document.
Courtney et al. "CRISPR/Cas9 DNA cleavage at SNP-derived PAM enables both in vitro and in vivo KRT12 mutation-specific targeting," Gene Therapy, Aug. 20, 2015 (Aug. 20, 2015), vol. 23, pp. 108-112. entire document.
Liang et al. "Rapid and highly efficient mammalian cell engineering via Cas9 protein transfection," Journal of Biotechnology, May 21, 2015 (May 21, 2015), vol. 208, pp. 44-53. entire document.
Smith et al. "Efficient and Allele-Specific Genome Editing of Disease Loci in Human iPSCs," Molecular Therapy, Dec. 16, 2014 (Dec. 16, 2014) vol. 23, pp. 570-577. entire document.
Svitashev et al. "Targeted Mutagenesis, Precise Gene Editing, and Site-Specific Gene Insertion in Maize Using CRs9 and Guide RNA." Plant Physiology, Aug. 12, 2015 (Aug. 12, 2015), vol. 169, pp. 931-945. entire document.
Wu et al. "Target specificity of the CRISPR-Cas9 system," Quantitative Biology, Aug. 26, 2014 (Aug. 26, 2014), vol. 2, Iss. 2, pp. 59-70. entire document.

* cited by examiner

*Primary Examiner* — Catherine S Hibbert
(74) *Attorney, Agent, or Firm* — Banner & Witcoff, Ltd.

(57) ABSTRACT

CRISPR/Cas Systems are provided where a tuned guide RNA is used to discriminate between two protospacer sequences of same length that differ by one nucleotide.

27 Claims, 16 Drawing Sheets

Specification includes a Sequence Listing.

Total reads

|  | Replicate number | | |
|---|---|---|---|
|  | 1 | 2 | 3 |
| TEM-1 | 140777 | 230440 | 99868 |
| TEM-1-S68N | 203786 | 175201 | 186887 |
| Diversity control | 140466 | 56107 | 147862 | bla.A203G.6A reads

|  | Replicate number | | |
|---|---|---|---|
|  | 1 | 2 | 3 |
| TEM-1 | 208 | 399 | 221 |
| TEM-1-S68N | 5642 | 2159 | 6386 |
| Diversity control | 20401 | 17074 | 20509 |

E

$$\text{bla.A203G.6A fraction} = \frac{\text{\# bla.A203G.6A reads}}{\text{\# total reads}}$$

bla.A203G.6A fractions

|  | Replicate number | | | |
|---|---|---|---|---|
|  | 1 | 2 | 3 | AVG |
| TEM-1 | 0.0015 | 0.0017 | 0.0022 | 0.0018 |
| TEM-1-S68N | 0.1001 | 0.0974 | 0.1097 | 0.1024 |
| Diversity control | 0.0401 | 0.0384 | 0.0431 | 0.0406 |

F

$$\text{bla.A203G.6A enrichment} = \frac{\text{bla.A203G.6A exp fraction}}{\text{bla.A203G.6A control fraction}}$$

bla.A203G.6A enrichments

|  | Fold enrichment |
|---|---|
| TEM-1 | 0.0044 |
| TEM-1-S68N | 2.522 |
| Diversity control | 1.000 |

Fig. 6D-F

CAS DISCRIMINATION USING TUNED GUIDE RNA

RELATED APPLICATION DATA

This application is a National Stage Application under 35 U.S.C. 371 of co-pending PCT application PCT/US16/66499 designating the United States and filed Dec. 14, 2016; which claims the benefit of U.S. provisional application No. 62/266,851 and filed Dec. 14, 2015 each of which are hereby incorporated by reference in their entireties.

STATEMENT OF GOVERNMENT INTERESTS

This invention was made with government support under HG005550 and CA009216 awarded by the National Institutes of Health. The government has certain right in the invention.

SEQUENCE LISTING

The instant application contains a Sequence Listing which has been submitted electronically in ASCII format and is hereby incorporated by reference in its entirety. Said ASCII copy, created on Dec. 14, 2016, is named "Sequence_Listing_010498_00893_5T25.txt," and is 20,401 bytes in size.

BACKGROUND

The CRISPR type II system is a recent development that has been efficiently utilized in a broad spectrum of species. See Friedland, A. E., et al., Heritable genome editing in *C. elegans* via a CRISPR-Cas9 system. Nat Methods, 2013. 10(8): p. 741-3, Mali, P., et al., RNA-guided human genome engineering via Cas9. Science, 2013. 339(6121): p. 823-6, Hwang, W. Y., et al., Efficient genome editing in zebrafish using a CRISPR-Cas system. Nat Biotechnol, 2013, Jiang, W., et al., RNA-guided editing of bacterial genomes using CRISPR-Cas systems. Nat Biotechnol, 2013, Jinek, M., et al., RNA-programmed genome editing in human cells. eLife, 2013. 2: p. e00471, Cong, L., et al., Multiplex genome engineering using CRISPR/Cas systems. Science, 2013. 339(6121): p. 819-23, Yin, H., et al., Genome editing with Cas9 in adult mice corrects a disease mutation and phenotype. Nat Biotechnol, 2014. 32(6): p. 551-3. CRISPR is particularly customizable because the active form consists of an invariant Cas9 protein and an easily programmable guide RNA (gRNA). See Jinek, M., et al., A programmable dual-RNA-guided DNA endonuclease in adaptive bacterial immunity. Science, 2012. 337(6096): p. 816-21. Of the various CRISPR orthologs, the *Streptococcus* pyogenes (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the gRNA and target DNA proceeds in a ratchet mechanism to form an R-loop. Following formation of a ternary complex of Cas9, gRNA, and target DNA, the Cas9 protein generates two nicks in the target DNA, creating a double-strand break (DSB) that is predominantly repaired by the non-homologous end joining (NHEJ) pathway or, to a lesser extent, template-directed homologous recombination (HR). CRISPR methods are disclosed in U.S. Pat. Nos. 9,023,649 and 8,697,359. See also, Fu et al., Nature Biotechnology, Vol. 32, Number 3, pp. 279-284 (2014). Additional references describing CRISPR-Cas9 systems including nuclease null variants (dCas9) and nuclease null variants functionalized with effector domains such as transcriptional activation domains or repression domains include J. D. Sander and J. K. Joung, *Nature biotechnology* 32 (4), 347 (2014); P. D. Hsu, E. S. Lander, and F. Zhang, *Cell* 157 (6), 1262 (2014); L. S. Qi, M. H. Larson, L. A. Gilbert et al., *Cell* 152 (5), 1173 (2013); P. Mali, J. Aach, P. B. Stranges et al., *Nature biotechnology* 31 (9), 833 (2013); M. L. Maeder, S. J. Linder, V. M. Cascio et al., *Nature methods* 10 (10), 977 (2013); P. Perez-Pinera, D. D. Kocak, C. M. Vockley et al., *Nature methods* 10 (10), 973 (2013); L. A. Gilbert, M. H. Larson, L. Morsut et al., *Cell* 154 (2), 442 (2013); P. Mali, K. M. Esvelt, and G M. Church, *Nature methods* 10 (10), 957 (2013); and K. M. Esvelt, P. Mali, J. L. Braff et al., *Nature methods* 10 (11), 1116 (2013).

SUMMARY

Embodiments of the present disclosure are directed to methods of designing and using a guide RNA that will discriminate between a target protospacer sequence and a nontarget sequence. According to one aspect, the target protospacer sequence and the nontarget sequence are of same length and differ by one nucleotide or by two nucleotides. According to one aspect, the target protospacer sequence is associated with a target nucleic acid and the nontarget sequence, such as a nontarget protospacer sequence, is associated with a nontarget nucleic acid. The guide RNA may be referred to herein as a "tuned guide RNA" to the extent that the spacer sequence of the guide RNA has been designed to discriminately bind to the target protospacer sequence versus the nontarget sequence. In this aspect, when the tuned guide RNA is used with a Cas enzyme, the Cas enzyme will cleave the target nucleic acid sequence associated with the target protospacer sequence and will not cleave the nucleic acid sequence associated with the nontarget sequence.

For purposes of the present disclosure, the protospacer sequence may be referred to as the double stranded sequence targeted by the guide RNA spacer sequence. While the guide RNA spacer sequence will bind to one strand of the protospacer sequence, i.e. the complement of the guide RNA spacer, the sequence of the guide RNA spacer may be described with respect to either strand of the protospacer sequence. For example, the guide RNA spacer sequence may be described as being complementary to one strand of the protospacer sequence while the guide RNA spacer sequence may be described as being identical to the other strand of the protospacer sequence. Accordingly, guide RNA spacer sequences may be described as being designed with respect to either strand. Should a guide RNA spacer sequence be described as being identical to a protospacer sequence, it is to be understood that the guide RNA spacer sequence is being designed with respect to the protospacer strand to which it will not bind. In this manner, the resulting guide RNA spacer sequence will bind to the other protospacer strand to which it is complementary.

Aspects of the present disclosure are useful for Cas discrimination of one target nucleic acid from another, such as where two or more or a plurality of nucleic acid sequences are similar in structure, such as alleles or nucleic acid sequences including one or more mutations or polymorphisms. Methods are provided for the Cas cleavage or cutting of a sequence that may be undesirable while maintaining the similar desirable sequence. Such aspects have utility in eliminating mutations that may occur in an organism. Accordingly, reference may be made to a "desired sequence" which is the DNA sequence to be preserved and not cut or cleaved with the Cas/guide RNA systems described herein. Reference may be made to an "undesired sequence" which is the DNA sequence to be cut or cleaved with the Cas/guide RNA systems described herein. According to one aspect, the protospacer sequence corresponding to the "undesired sequence" and the protospacer corresponding to the "desired sequence" may be of the same length and may differ by a single nucleotide change. In this manner, a guide RNA spacer sequence may be designed or "tuned" to direct a Cas protein to the protospacer corresponding to the undesired sequence for cutting or cleaving of the undesired sequence while not directing a Cas protein to the protospacer sequence corresponding to the desired sequence. In this manner, a Cas/guide RNA system may be provided to a cell which will direct cutting or cleaving of a target mutation of a desired sequence that may occur within the cell. Such cutting or cleaving may result in cell death. Such cutting or cleaving may result in genomic alteration of the cell. Such cutting or cleaving may result in altering of expression of the target nucleic acid, such as lowering expression of the target nucleic acid.

The tuned guide RNA may be described as being discriminatory to the extent that the Cas9/gRNA system discriminates between the desired and undesired target sequences. A system is said to be "completely discriminatory" if it cuts or cleaves the undesired sequence at 100% efficiency, and the desired sequence at 0% efficiency. A system with "high discriminatory power" would be one that exhibits greater that 90% efficiency against the undesired sequence and less than 10% efficiency against the desired sequence.

Target sequences as described herein may be endogenous or exogenous. An endogenous target is one that exists on the genomic (or otherwise endogenous, e.g., mitochondrial) DNA of the host organism in which the system is provided. An exogenous target sequence is one that does not exist on the genomic (or otherwise endogenous, e.g., mitochondrial) DNA of the host organism in which the system is provided. An exogenous target sequence is one that is nonnaturally occurring within the cell and which may be provided as a plasmid introduced to the cell or a transiently transfected DNA element.

A Cas as described herein may be any Cas known to those of skill in the art that may be directed to a target nucleic acid using a guide RNA as known to those of skill in the art. The Cas may be wild type or a homolog or ortholog thereof. The Cas may be nonnaturally occurring, such as an engineered Cas. The Cas may have one or more nucleolytic domains altered to prevent nucleolytic activity, such as with a Cas nickase or nuclease null or "dead" Cas. Aspects of the present disclosure utilize nicking to effect cutting of one strand of the target nucleic acid. A nuclease null or "dead" Cas may have a nuclease attached thereto to effect cutting, cleaving or nicking of the target nuclease acid. Such nucleases are known to those of skill in the art.

Embodiments of the present disclosure are directed to methods of using an enzymatically active Cas, such as a Cas9 nuclease or nickase, and a guide RNA with a spacer sequence to bind to binds to a target nucleic acid and to form a complex, such as a co-localization complex, with the enzymatically active Cas and the target nucleic acid, and sufficient to allow the enzymatically active Cas to function as a nuclease or nickase with respect to the target nucleic acid. An enzymatically active Cas may refer to the Cas itself or a Cas with a nuclease attached thereto.

Aspects of the present disclosure are directed to programmable genome editing as an enzymatically active Cas9 can be used to cut or nick a target nucleic acid having a mutated target protospacer sequence by using a tuned guide RNA spacer sequence that targets the mutated protospacer sequence but does not target the normal, nonmutated protospacer sequence. In this manner, a Cas/guide RNA system is provided that can discriminate between a target protospacer sequence that differs by a single nucleotide.

According to certain aspects, the Cas protein may be provided to the cell as a native protein. According to certain aspects, the Cas protein may be provided to the cell as a nucleic acid which is expressed by the cell to provide the Cas protein. According to certain aspects, the guide RNA may be provided to the cell as a native guide RNA. According to certain aspects, the guide RNA may be provided to the cell as a nucleic acid which is expressed by the cell to provide the guide RNA. According to certain aspects, a donor sequence may be provided to the cell which may be inserted at the cut or cleavage site. Accordingly, methods described herein contemplate the use of one or more donor nucleic acids that may be inserted into one or more cut or nick sites through homologous recombination or nonhomologous end joining. According to one aspect, a plurality of guide RNAs may be provided to the cell wherein the guide RNAs are directed to a plurality of target nucleic acid sequences.

According to certain aspects, a guide RNA includes a spacer sequence and a tracr mate sequence forming a crRNA, as is known in the art. According to certain aspects, a tracr sequence, as is known in the art, is also used in the practice of methods described herein. According to one aspect, the tracr sequence and the crRNA sequence may be separate or connected by the linker, as is known in the art. According to one aspect, the tracr sequence and the crRNA sequence may be a fusion.

According to one aspect, the Cas protein is expressed by the cell. According to one aspect, the Cas protein is naturally occurring within the cell. According to one aspect, the Cas protein is provided to the cell by introducing into the cell a first foreign nucleic acid encoding the Cas protein, wherein the Cas protein is expressed. According to one aspect, the guide RNA is provided to the cell by introducing into the cell a second foreign nucleic acid encoding the guide RNA, wherein the guide RNA is expressed. The Cas protein and the guide RNA co-localize to the target nucleic acid.

According to one aspect, the Cas protein is an enzymatically active Cas9 protein that is fully enzymatic as is known in the art or a Cas9 protein nickase as is known in the art. According to one aspect, the cell is in vitro, in vivo or ex vivo. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, a human induced pluripotent stem cell, a plant cell or an animal cell. According to one aspect, the target nucleic acid is genomic DNA, mitochondrial DNA, plastid DNA, viral DNA, exogenous DNA or cellular RNA.

According to one aspect, a cell is provided, such as a genetically-modified cell, which includes an enzymatically active Cas9 and at least one tuned guide RNA including a spacer sequence and a tracr mate sequence forming a crRNA and a tracr sequence and wherein the tuned guide RNA and the enzymatically active Cas9 are members of a co-localization complex for the target nucleic acid. The tuned guide RNA is able to discriminate or discriminates between a normal nonmutated protospacer sequence and a mutant protospacer sequence which differs from the nonmutated spacer sequence by one nucleotide. According to one aspect, the Cas9 is nonnaturally occurring within the cell. According to one aspect, the tuned guide RNA is nonnaturally occurring within the cell. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, a human induced pluripotent stem cell, a plant cell or an animal cell.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 4A-C is directed to data demonstrating a screening method to identify tuned spacers that could effectively discriminate between the inactive TEM-1-N68 and the active TEM-1-S68.

FIG. 6A-I are directed to various aspects and data regarding a spacer screening process.

DETAILED DESCRIPTION

Figure 1:
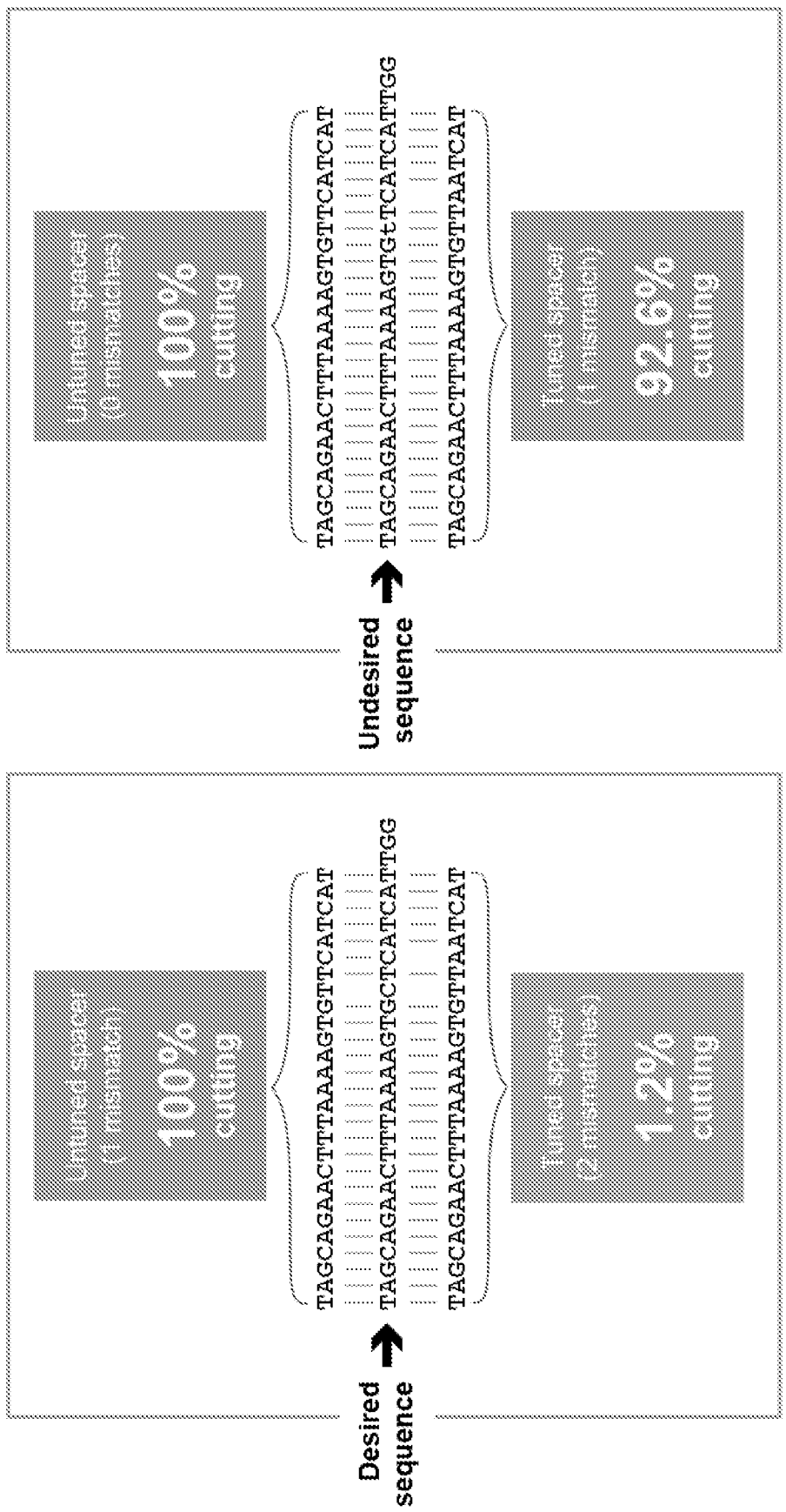
FIG. 1 is a schematic showing alteration of a spacer sequence to improve cutting of a target sequence and limit cutting of an off-target or non-target sequence. (SEQ ID NO:1-3)

Embodiments of the present disclosure are directed to the use of a CRISPR/Cas system and, in particular, a Cas9 protein, and one or more guide RNAs, each of which includes a spacer sequence, a tracr mate sequence and a tracr sequence. The guide RNA binds to a nucleic acid sequence called a "protospacer sequence" which may be associated with a PAM sequence and a target nucleic acid sequence as is known in the art.

Aspects of the present disclosure are based on the objective of altering a guide RNA spacer sequence that binds to a first target protospacer such that it no longer binds to the first target protospacer, but does bind to a second target protospacer that differs from the first target protospacer by one nucleotide or two nucleotides. The guide RNA spacer sequence may differ from the second target protospacer sequence by one or two nucleotides. The guide RNA spacer sequence may differ from the first target protospacer by two or three nucleotides. In this manner, a Cas system can provide a high degree of cutting or cleaving when the guide RNA binds to the second target protospacer and with a low degree of cutting or cleaving when the guide RNA binds to the first target protospacer. In this manner, the guide RNA may be designed to regulate binding capability to the first target protospacer and the second target protospacer. For example, the first target protospacer may be a normal protospacer while the second target protospacer may be a mutant or allele of the first target protospacer. The second target protospacer may include a single nucleotide polymorphism compared to the first target protospacer. The second target protospacer may include two single nucleotide polymorphisms compared to the first target protospacer. It is to be understood that alleles differ by one or more single nucleotide polymorphisms. Single nucleotide differences between the first target protospacer and the second target protospacer need not result from mutation.

According to one exemplary aspect, a guide RNA that includes a spacer sequence identical to the first target protospacer will bind to the first target protospacer. To design a guide RNA that binds to the second target protospacer having a single nucleotide polymorphism compared to the first target protospacer, the guide RNA includes a spacer sequence identical to the second target protospacer. Accordingly, the guide RNA spacer sequence for the second target protospacer includes a first nucleotide substitution compared to the guide RNA spacer sequence for the first target protospacer. The guide RNA spacer sequence for the second target protospacer is further designed to include a second nucleotide substitution compared to the guide RNA spacer sequence for the first target protospacer. With this design, the guide RNA spacer sequence for the second target protospacer sequence will preferentially bind to the second target protospacer and will not preferentially bind to the first target protospacer. Stated differently, the guide RNA spacer sequence for the second target protospacer sequence will bind to a greater extent to the second target protospacer and will bind to a lesser extent to the first target protospacer. The guide RNA spacer sequence for the second target protospacer has been designed to discriminate between two protospacer sequences that differ by one nucleotide. A guide RNA spacer sequence for the second target protospacer may be designed to discriminate between two protospacer sequences that differ by two nucleotides or three nucleotides. Accordingly, a discriminatory guide RNA spacer sequence is provided to the extent that the spacer sequence will bind to a mutant of a normal protospacer sequence and will not bind to the normal protospacer sequence, at least not to any significant extent compared to binding to the mutant of a normal protospacer sequence. Such a discriminatory guide RNA spacer sequence is useful to bind to protospacers having a single nucleotide polymorphism and to facilitate cutting of a corresponding nucleic acid sequence using a Cas protein.

According to certain aspects, a discriminatory guide RNA spacer sequence is provided to the extent that the spacer sequence will bind to first allele of a protospacer sequence and will not bind to the second allele of the protospacer sequence, at least not to any significant extent compared to binding to the first allele of the protospacer sequence. Such a discriminatory guide RNA spacer sequence is useful to bind to one allele of a protospacer having a single nucleotide difference with another allele of a protospacer and to facilitate cutting of a corresponding nucleic acid sequence using a Cas protein.

According to certain aspects, a guide RNA within the scope of the present disclosure discriminates between a target protospacer sequence and a nontarget sequence which differs from the target protospacer sequence by one nucleotide or by two nucleotides. The guide RNA may be designed for single nucleotide specificity between protospacer sequences. Such a guide RNA, which may be called a "tuned guide RNA," is designed to distinguish between nucleic acid sequences of same length having similar sequences of nucleotides for purposes of binding and forming a co-localization complex with Cas and a target nucleic acid. Nucleic acid sequences of same length may be similar to the extent that they differ by one nucleotide or two nucleotides.

Exemplary methods are described herein where a spacer sequence is modified to increase its ability to discriminate between a first protospacer sequence and a second protospacer sequence where the second protospacer sequence may be an intended target and the first protospacer sequence may be an off-target sequence that differs by one nucleotide or two nucleotides. According to certain aspects, a tuned guide RNA may discriminate between a target protospacer sequence and a second or nontarget protospacer sequence where the target protospacer sequence is a single nucleotide mutation of the nontarget protospacer sequence. In this aspect, the tuned guide RNA will bind to the mutant protospacer sequence, i.e. the target protospacer sequence, and facilitate Cas cleavage of the target nucleic acid associated with the mutant protospacer sequence. In this aspect, the tuned guide RNA will not bind to the normal or nonmutated protospacer sequence. In one aspect, the tuned guide RNA has insignificant binding to the normal or nonmutated protospacer sequence. In this aspect, the cell in which the tuned guide RNA is provided along with a Cas enzyme includes a system that can cleave a target nucleic acid if the normal protospacer sequence mutates to a sequence to which the tuned guide RNA can bind. In this manner, embodiments of guide RNA and Cas systems are provided in methods of achieving single nucleotide endonucleolytic specificity. According to this exemplary aspect, if a single nucleotide or point mutation occurs in a cell having a tuned guide RNA/Cas system, the tuned guide RNA can bind to the sequence including the single nucleotide or point mutation and the Cas can cleave the target nucleic acid associated with the protospacer sequence including the single nucleotide or point mutation. According to this aspect, the tuned guide RNA/Cas system acts as a surveillance system to the extent that it reacts to occurrence of a point mutation insofar as the tuned guide RNA will bind to the sequence including the point mutation to facilitate Cas cleavage or cutting of the target nucleic acid associated with the sequence including the point mutation.

According to one aspect, methods are described of tuning or altering a spacer sequence to increase the ability of the spacer sequence to discriminate between an intended target sequence and an off-target sequence that differs by one nucleotide or by two nucleotides. For exemplary purposes, a target sequence may be a sequence that includes a single nucleotide polymorphism or two single nucleotide polymorphisms compared to the off-target sequence, as one aspect of the present disclosure is to target a CRISPR Cas guide RNA system to mutations in a nucleic acid sequence. According to one aspect, a gRNA includes a spacer sequence that is perfectly complementary to the target sequence and has a single nucleotide difference from the off-target sequence. Such a guide RNA may exhibit cutting at the off-target sequence. According to methods described herein, the tuning process includes introducing additional one or more mutations in the spacer sequence, such that it has n mismatches with the target sequence, and n+1 or more mismatches with the off-target sequence. As a result, a spectrum of cutting efficiencies allowing for single-nucleotide discrimination is achieved. Table 1 indicates exemplary relative representative cutting percentages based on mismatch numbers.

| Num. of mismatches against target | Num. of mismatches against off-target | Percent cutting of target | Percent cutting of off-target |
|---|---|---|---|
| 0 | 1 | 100% | 100% |
| 1 | 2 | 98% | 2% |
| 2 | 3 | 34% | 0% |
| 3 | 4 | 0% | 0% |

As exemplified in the above Table, introducing either one or two mutations may result in sufficient discriminatory power for most applications requiring single nucleotide discrimination.

Aspects of the present disclosure also include methods of screening for suitable tuned guide RNAs as described herein having spacers with high discriminatory ability. According to one aspect, methods include determining relative enrichment of spacer sequences in the presence of the target and off-target sequences. An exemplary screen involves 3 biological replicates of the following conditions:
1) [strain containing endogenous off-target]+tgRNA library
2) [strain containing endogenous off-target]+tgRNA library+Cas9
3) [strain containing endogenous off-target]+tgRNA library+Cas9+plasmid containing target sequence A library of candidate tuned guide RNAs ("tgRNA library") is prepared. An orthogonal spacer control may be included in the tgRNA library. Condition (1) controls for spacer representation in the library. Condition (2) is used to measure the relative enrichment of tgRNA candidates in the presence of the off-target. Spacers that do not cut the off-target should have a relative fold-enrichment of >=1. Condition (3) is used to measure the relative enrichment of tgRNA candidates in the presence of the target sequence. When condition (3) is normalized to condition (2), tgRNA candidates that have a relative fold-enrichment of <1 are those that exhibit active cutting of the target.

Figure 4:
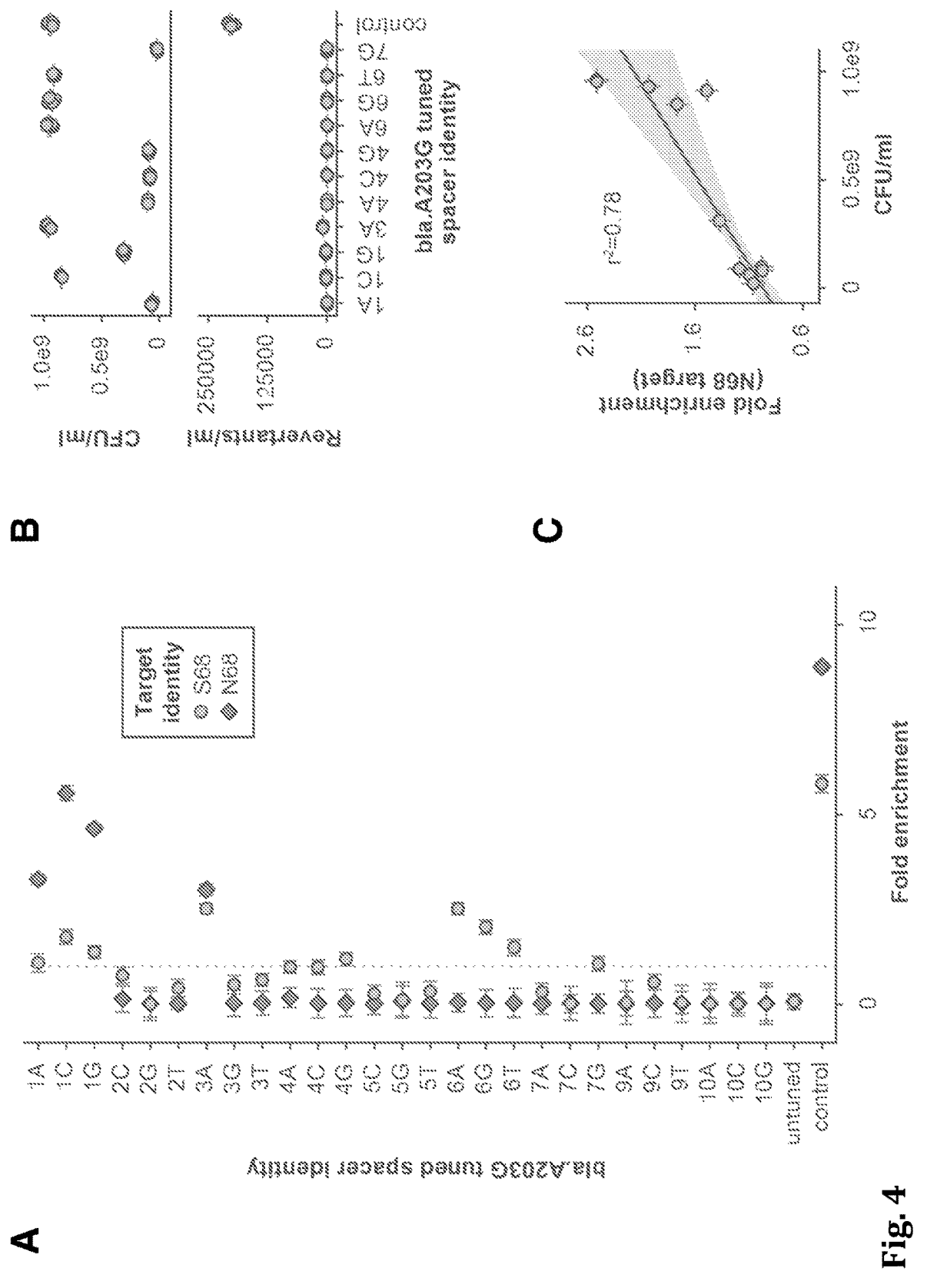

In the case of exogenous targets (e.g., plasmid-encoded TEM-1, as in FIG. 4), an exemplary method of screening is as follows:
1) [standard strain background]+tgRNA library
2) [standard strain background]+tgRNA library+Cas9+plasmid containing off-target sequence
3) [standard strain background]+tgRNA library+Cas9+plasmid containing target sequence In this case, normalization of condition (2) to condition (1) and condition (3) to condition (1) measures the cut rates of the library against the off-target, and target sequences, respectively.

Methods of cleaving mutations are described herein. A Cas9-tgRNA system may be used to cleave mutations after they occur in living cells. In most embodiments, Cas9 and the tgRNA will be provided to the cell, such as by being expressed inside the target cell population (exogenously from a plasmid/virus, or endogenously) or will be provided as native species using methods known to those of skill in the art of introducing proteins and native nucleic acid sequences to cells. Once produced or being present inside the cell, Cas9-tgRNA will exhibit no cutting against the off-target. If the target mutation occurs, the Cas9-tgRNA system will cut at the target site, resulting in the removal of the mutation containing sequence from the population (and in some cases, cell death). In cases where Cas9 cutting may be repaired by endogenous repair enzymes, a replacement template, i.e. donor nucleic acid, with toxic or otherwise deleterious effects may be provided as part of the system, should cell death desired.

Methods described herein can be used to cleave exogenous nucleic acids. Methods described herein can be used to cleave endogenous nucleic acids. Methods described herein can be used with known Cas proteins or orthologs or engineered versions thereof. Methods described herein can be practiced in vivo, ex vivo or in vitro. Methods described herein can be multiplexed within a single target nucleic acid region or across multiple regions.

According to certain aspects, an exemplary spacer sequence is between 10 and 30 nucleotides in length. According to certain aspects, an exemplary spacer sequence is between 15 and 25 nucleotides in length. An exemplary spacer sequence is between 18 and 22 nucleotides in length. An exemplary spacer sequence is 20 nucleotides in length. According to certain methods, two or more or a plurality of guide RNAs may be used in the practice of certain embodiments.

The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. A CRISPR complex may include the guide RNA and the Cas9 protein. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

Tracr mate sequences and tracr sequences are known to those of skill in the art, such as those described in US 2014/0356958. The tracr mate sequence and tracr sequence used in the present disclosure is N20 to N8-gttt-tagagctagaaatagcaagttaaaataaggctagtccgttatcaactt-gaaaaagtggcaccgagtcggtgctttttt (SEQ ID NO:4) with N20-8 being the number of nucleotides complementary to a target locus of interest.

According to certain aspects, the tracr mate sequence is between about 17 and about 27 nucleotides in length. According to certain aspects, the tracr sequence is between about 65 and about 75 nucleotides in length. According to certain aspects, the linker nucleic acid sequence is between about 4 and about 6.

According to one aspect, embodiments described herein include guide RNA having a length including the sum of the lengths of a spacer sequence, tracr mate sequence, tracr sequence, and linker sequence (if present). Accordingly, such a guide RNA may be described by its total length which is a sum of its spacer sequence, tracr mate sequence, tracr sequence, and linker sequence. According to this aspect, all of the ranges for the spacer sequence, tracr mate sequence, tracr sequence, and linker sequence (if present) are incorporated herein by reference and need not be repeated. One of skill will readily be able to sum each of the portions of a guide RNA to obtain the total length of the guide RNA sequence. Aspects of the present disclosure are directed to methods of making such guide RNAs as described herein by expressing constructs encoding such guide RNA using promoters and terminators and optionally other genetic elements as described herein.

According to certain aspects, the cell includes a naturally occurring Cas protein. According to certain aspects, the guide RNA and the Cas protein which interacts with the guide RNA are foreign to the cell into which they are introduced or otherwise provided. According to this aspect, the guide RNA and the Cas protein are nonnaturally occurring in the cell in which they are introduced, or otherwise provided. To this extent, cells may be genetically engineered or genetically modified to include the CRISPR/Cas systems described herein.

Exemplary Cas protein include *S. pyogenes* Cas9, *S. thermophilus* Cas9 and *S. aureus* Cas9. One exemplary CRISPR/Cas system uses the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). The DNA locus targeted by Cas9 precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 to a target nucleic acid. In a multitude of CRISPR-based biotechnology applications, the guide is often presented in a so-called sgRNA (single guide RNA), wherein the two natural Cas9 RNA cofactors (gRNA and tracrRNA) are fused via an engineered loop.

Embodiments of the present disclosure are directed to a method of delivering an enzymatically active Cas9 protein to a target nucleic acid in a cell comprising providing to the cell the enzymatically active Cas9 protein and a guide RNA having a tuned spacer sequence as described herein wherein the guide RNA and the Cas9 protein form a co-localization complex with the target nucleic acid and where the enzymatically active Cas9 protein cuts or cleaves the target nucleic acid. Methods described herein can be performed in vitro, in vivo or ex vivo. According to one aspect, the cell is a eukaryotic cell or a prokaryotic cell. According to one aspect, the cell is a bacteria cell, a yeast cell, a mammalian cell, a human cell, a stem cell, a progenitor cell, an induced pluripotent stem cell, a human induced pluripotent stem cell, a plant cell or an animal cell. According to one aspect, the Cas9 protein is an enzymatically active Cas9 protein, a Cas9 protein wild-type protein, or an enzymatically active Cas9 nickase. Additional exemplary Cas9 proteins include Cas9 proteins attached to, bound to or fused with a nuclease such as a Fok-domain, such as Fok 1 and the like. Exemplary nucleases are known to those of skill in the art.

According to certain aspects, the Cas protein may be delivered directly to a cell as a native species by methods known to those of skill in the art, including injection or lipofection, or as translated from its cognate mRNA, or transcribed from its cognate DNA into mRNA (and thereafter translated into protein). Cas DNA and mRNA may be themselves introduced into cells through electroporation, transient and stable transfection (including lipofection) and viral transduction or other methods known to those of skill in the art. According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to certain aspects, a first nucleic acid encoding an enzymatically active Cas9 is provided to a cell. A second nucleic acid encoding a tuned guide RNA having a spacer sequence complementary to the target protospacer sequence for a target nucleic acid, is provided to the cell. The cell expresses the guide RNA and the enzymatically active Cas9, wherein the guide RNA and the Cas9 protein form a co-localization complex with the target nucleic acid. According to one aspect, the enzymatically active Cas9 cuts or nicks the target nucleic acid. According to one aspect, the first nucleic acid encoding the Cas9 protein and the second nucleic acid encoding the guide RNA may be present on the same or different vectors. The cell may be any desired cell including a eukaryotic cell. An exemplary cell is a human cell. An exemplary cell is a stem cell, whether adult or embryonic. An exemplary cell is an induced pluripotent stem cell. An exemplary cell is an embryonic stem cell. According to this aspect, the embryonic stem cell which may then be implanted into an animal where the embryonic stem cell differentiates into a particular desired tissue type and the tissue type expresses the nucleic acids encoding the Cas9 and the guide RNA.

Embodiments of the present disclosure are directed to a method of delivering an enzymatically active Cas9 protein to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a enzymatically active Cas9 protein or a nucleic acid encoding the enzymatically active Cas9 protein.

Embodiments of the present disclosure are directed to a method of delivering a tuned guide RNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a tuned guide RNA or a nucleic acid encoding the tuned guide RNA.

Embodiments of the present disclosure are directed to a method of delivering an enzymatically active Cas9 protein and a tuned guide RNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, an enzymatically active Cas9 or a nucleic acid encoding the enzymatically active Cas9 protein and a tuned guide RNA or a nucleic acid encoding the tuned guide RNA.

Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety. In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. Nucleic acids research 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus. Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermo-*

*philus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus*. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis*; *Francisella tularensis* WY96-3418; and *Treponema denticola* ATCC 35405. The Cas9 protein may be referred by one of skill in the art in the literature as Csn1. An exemplary *S. pyogenes* Cas9 protein sequence is shown below. See Deltcheva et al., *Nature* 471, 602-607 (2011) hereby incorporated by reference in its entirety.

```
                                          (SEQ ID NO: 5)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL
```

```
TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEREQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD.
```

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to one aspect, a Cas9 protein having two or more nuclease domains may be modified or altered to inactivate all but one of the nuclease domains. Such a modified or altered Cas9 protein is referred to as a nickase, to the extent that the nickase cuts or nicks only one strand of double stranded DNA. According to one aspect, the Cas9 protein or Cas9 protein nickase includes homologs and orthologs thereof which retain the ability of the protein to bind to the DNA and be guided by the RNA. According to one aspect, the Cas9 protein includes the sequence as known for naturally occurring Cas9 proteins, such as that from *S. pyogenes*, *S. thermophilus* or *S. aureus* and protein sequences having at least 30%, 40%, 50%, 60%, 70%, 80%, 90%, 95%, 98% or 99% homology thereto and being a DNA binding protein, such as an RNA guided DNA binding protein.

Target nucleic acids include any nucleic acid sequence to which a co-localization complex as described herein can be useful to either cut, nick, regulate, identify, influence or otherwise target for other useful purposes using the methods described herein. Target nucleic acids include cellular RNA. Target nucleic acids include cellular DNA. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" or "operatively linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The following examples are set forth as being representative of the present disclosure. These examples are not to be construed as limiting the scope of the present disclosure as these and other equivalent embodiments will be apparent in view of the present disclosure, figures and accompanying claims.

Example I

Method of Altering a Spacer Sequence to Improve Discrimination Between a Target Sequence and an Off Target Sequence Aspects of the present disclosure use the following spacer sequence naming convention:
<gene/locus name>.<target mutation>.<spacer mutations, negatively indexed>

For example, rpob.T1534C.4A is a spacer sequence that targets the mutation of the thymine at position 1534 to a cytosine in the rpoB gene. The spacer contains the additional mutation 4A, which means that the fourth base from the PAM-end of the spacer (negatively indexed) is mutated to an adenine.

(SEQ ID NO: 6)
5'-[NNNNNNNNNNNNNNNNXNNN] [PAM]

X—4$^{th}$ base from the PAM-end

FIG. 1 is a schematic showing alteration of a spacer sequence to improve cutting of a target sequence and limit cutting of an off-target or non-target sequence. In this instance, the "undesired" sequence is the sequence including the mutation. The "desired" sequence is the normal or nonmutated sequence. A spacer sequence identical to the undesired sequence and having one mismatch with the desired sequence is provided with a mismatch to the undesired sequence, thereby providing two mismatches to the desired sequence. The introduction of a mismatch at the "6" position results in near-perfect discrimination between the desired and undesired sequences. Introducing mutations in the spacer sequence as described herein produces guide RNA with spacer sequences exhibiting minimal cutting of the desired/off-target sequence (which does not contain the target SNP/mutation, for example) and maximal cutting of the undesired/target sequence (which contains the target SNP/mutation, for example).

Figure 2:
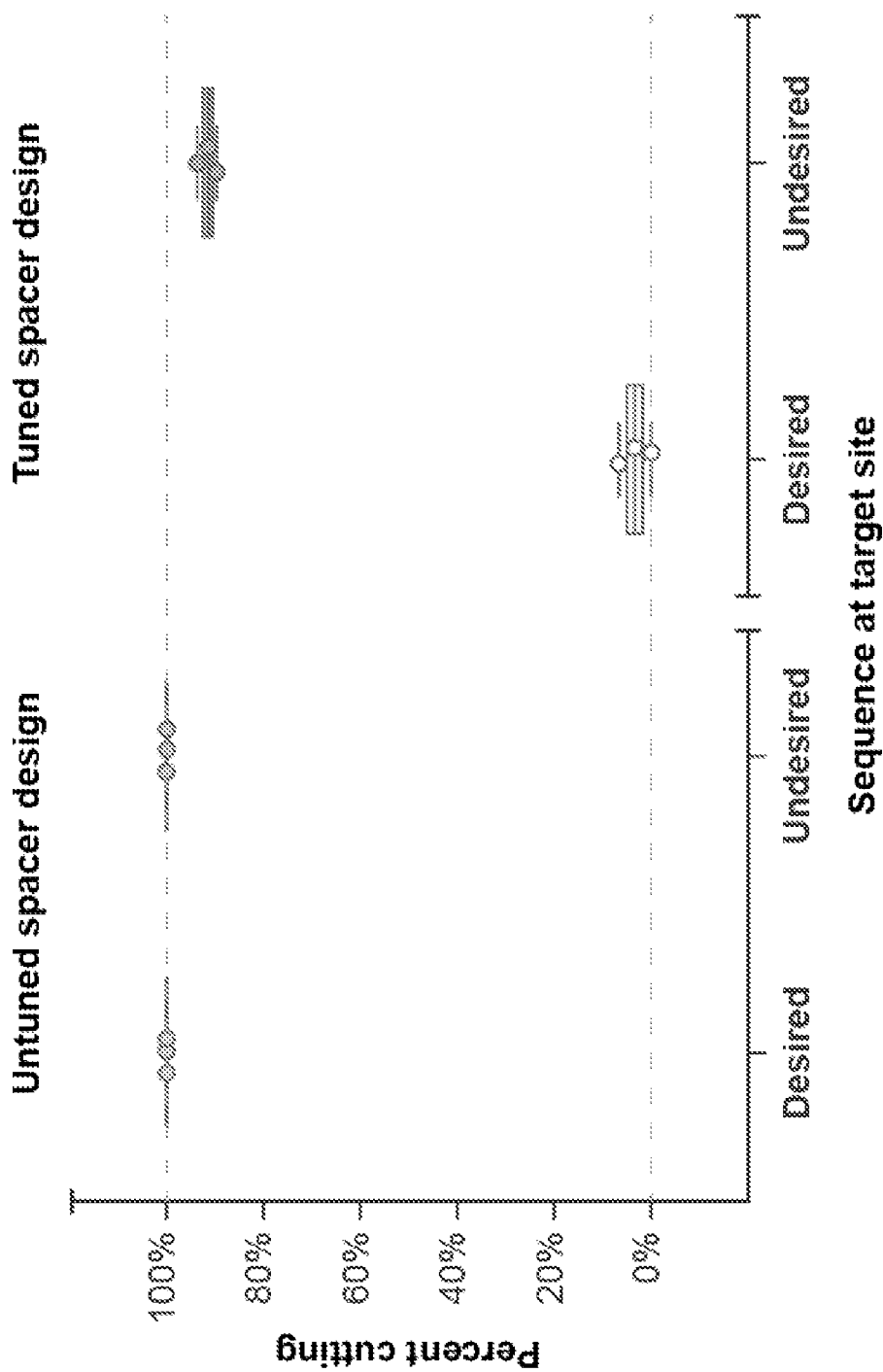
FIG. 2 is a graph showing the effect of tuning a guide RNA on the cutting of a target nucleic acid associated with a desired sequence and an undesired sequence.

FIG. 2 shows the effect of tuning a guide RNA on the cutting of a target nucleic acid associated with a desired sequence and an undesired sequence. Introduction of Cas9+ gRNA to cells containing either the desired target sequence (no mutation) or the undesired target sequence (single point mutation) demonstrates the importance of spacer tuning for proper discrimination, as the tuned guide RNA will direct Cas9 to cut the undesired sequence and not the desired sequence. Percent cutting is calculated as the reciprocal of post-transformation cell viability (n=3, error bars are SEM).

Example II

Figure 3A:
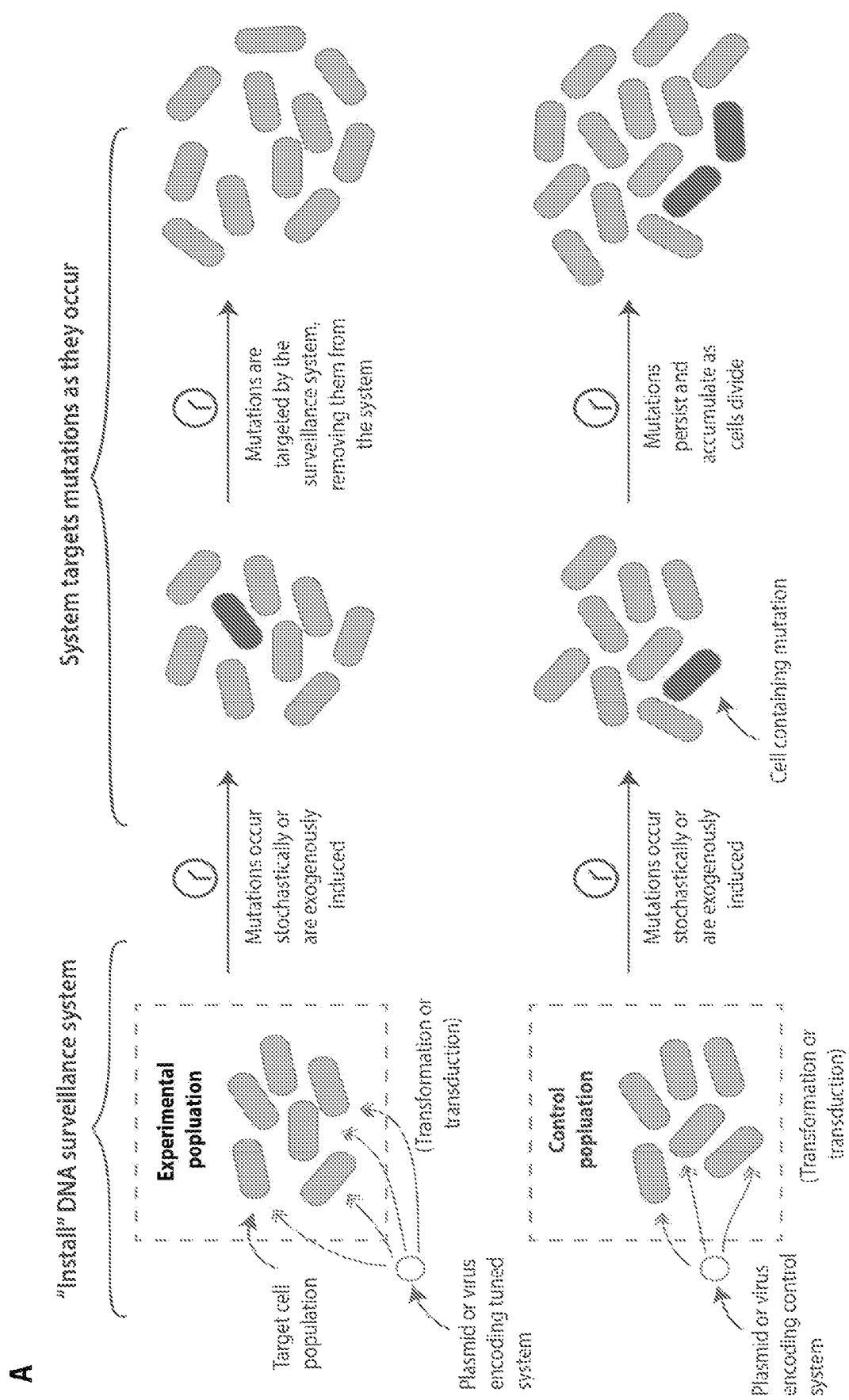
FIG. 3A-B is a schematic showing a method of providing cells with a guide RNA having a tuned spacer sequence and a Cas protein where the tuned spacer sequence binds to a mutant protospacer sequence.
Figure 3B:
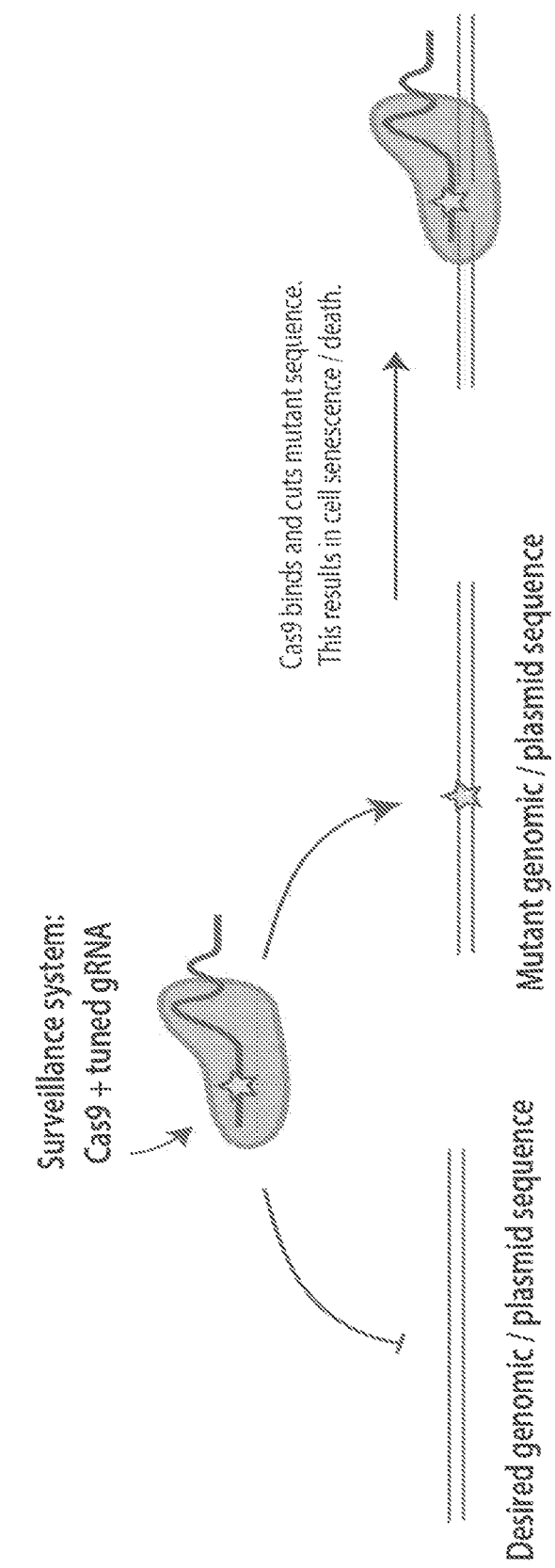

Method of Cleaving Nucleic Acid Sequences Associated with a Mutated Protospacer Sequence FIG. 3A-B is a schematic showing a method of providing cells with a guide RNA having a tuned spacer sequence and a Cas protein where the tuned spacer sequence binds to a mutant protospacer sequence. A system including a tuned gRNA (tgRNA) and Cas9 or a Cas9 ortholog is inserted into a population of cells via transformation or transduction (FIG. 3A). Cas9 and the tgRNA are expressed and form complexes within the cell population. Over the lifetime of the cells, mutations occur stochastically as genomic/plasmid DNA is replicated. If the targeted mutation occurs, the Cas9 guided by the tgRNA will cut at the target locus, resulting in plasmid or genome loss, and cell death (FIG. 3B). As a result, mutations will not accumulate in the cell population containing the system, but will accumulate in a wild type or control population.

Example III

Method of Screening for a Tuned Guide RNA

TEM-1 is a beta-lactamase that confers β-lactam antibiotic resistance to *E. coli*. A catalytically inactive version of TEM-1 was generated in which the active site serine (S68) was mutated to an arginine (N68) through a single nucleotide mutation (G203A). Spacers were screened to identify tuned spacers that could effectively discriminate between the inactive TEM-1-N68 and the active TEM-1-S68 (FIG. 4A). A fold enrichment below 1 indicates that the respective Cas9-tgRNA system cut into the target. Well-tuned guides have a fold enrichment of <1 for the S68 target (equating high cutting activity against the non-desired sequence) and a fold enrichment of >1 for the N68 target (equating minimal to no cutting against the desired sequence). After identifying putatively effective tgRNAs, a subset was tested for background cutting and mutation prevention capabilities (FIG. 4B). Four of the eleven guides exhibited both minimal background cutting (evidenced by near-control levels of CFU/ml) and good mutation prevention (evidenced by near-zero levels of revertants/ml) (FIG. 4C). The level of tgRNA enrichment from the screen performed in the presence of N68 (the desired sequence) was inversely correlated with background cutting. Properly tuned gRNAs will not cut the desired N68 sequence and thus will not cause a loss of CFUs. Well-tuned tgRNA will have the highest fold enrichment against the desired sequence, with a <1 fold enrichment against the undesired sequence. (A: n=3, B: n=5, C: n=3/5; all error bars are SEM).

bla.A203G Screen Materials and Methods
Golden Gate Reactions

All golden gate reactions were performed in the same manner. If not already hybridized, insert heteroduplexes were formed by adding 9 ul of each single stranded component to 2 ul of 10×T4 DNA ligase buffer (NEB #B0202S), heating to 95 C for 1 minute, and then ramping to 23 C at a rate of 0.1 C/second. Each golden gate reaction was assembled as follows: 40 fmol of each insert heteroduplex, 20 ng of backbone plasmid (e.g., pMSPACER-GG), 1 ul of ATP (NEB #P0756L), 1 ul of 10× CutSmart buffer (NEB #B7204S), 0.5 ul Sapl (NEB #R0569L), 0.5 ul T4 DNA Ligase (LC, NEB #M0202L), and nuclease free water to a total volume of 10 ul. Reactions were subjected to the following thermocycling protocol: 37 C for 2 hours, 50 C for 5 minutes, 80 C for 15 minutes. Following thermocycling, 1 ul of the resulting solution was transformed into 15 ul of chemically competent *E. coli* DH5a following the manufacturer's protocol (NEB #C2987H). Cells were allowed to recover for 1 hour at 37 C in 500 ul of SOC. The entire recovery was plated to selective media. Individual colonies were picked and sent out for Sanger sequencing confirmation using appropriate primers.

Spacer Library Plasmids Construction

Spacer library members were constructed using golden gate cloning in conjunction with the compatible pMSPACER-GG plasmid. For each spacer sequence, two oligonucleotides (oligos) were ordered from IDT such that the heteroduplex resulting from their hybridization constituted an appropriate golden gate insert. For example:

```
GFP control spacer sequence:
                                          (SEQ ID NO: 7)
ACTACAAGACACGTGCTGAAGTCAAGTTTG GFP control insert A:
                                          (SEQ ID NO: 8)
ggtt ACTACAAGACACGTGCTGAAGTCAAGTTTG g GFP control insert B:
                                          (SEQ ID NO: 9)
aaac CAAACTTGACTTCAGCACGTGTCTTGTAGT a Heteroduplex:
                                         (SEQ ID NO: 10)
ggtt ACTACAAGACACGTGCTGAAGTCAAGTTTG g
   a TGATGTTCTGTGCACGACTTCAGTTCAAAC caaa
```

Upon receipt, oligonucleotides were resupended to a final concentration of 100 uM in TE buffer. Golden gate cloning was then performed as described in "Golden gate reactions." Sequence verification was performed using primer PAC716 (see Table 2).

Target Plasmid Construction

Target plasmids for the bla.A203G spacer screen were constructed as derivatives of the pMTARGET-GG plasmid. Briefly, a DNA cassette encoding the $P_{ampR}$ promoter driving expression of a functional TEM-1 F70G variant, referred to as TEM-1 was cloned into the pMTARGET backbone. TEM-1, when expressed confers resistance to ampicillin. Site directed mutagenesis was then performed to create the derivative pMTARGET-TEM1-S68N from pMTARGET-TEM1. The serine at amino acid position 68 was converted into an arginine by introducing the A203G nucleotide substitution, this S68N mutation renders TEM-1 non-functional.

Spacer Library Strain Construction

The *E. coli* strains necessary for the bla.A203G spacer screen were constructed as derivatives of wild type MG1655 *E. coli*. The following strains were constructed through standard electrocompetent cell transformations (pMDCAS9 is a version of pMCAS9 in which Cas9's nuclease activity has been inactivated through the introduction of the canonical H840A and D10A amino acid substitutions):
MG1655+pMCAS9+pMSPACER bla.A203G library
MG1655+pMDCAS9+pMSPACER bla.A203G library Spacer Library Screen The general principle underlying the screen is that cells harboring a Cas9/gRNA system exhibiting activity against a given desired or undesired target sequence will be selected against in a mixed population, under conditions which select for the maintenance of the Cas9/gRNA system. As a result, the relative enrichment/de-enrichment of a given spacer species in the presence of the target can be used as a direct readout of the spacer's activity against the target.

The spacer library screen was performed using the pMTARGET bla.A203G library strains harboring either pMCAS9 or pMDCAS9, as described above. For each of the described conditions, three biological replicates were prepared and analyzed in parallel.

The following strains were generated from the progenitors described in "Spacer library strain construction":
A: MG1655+pMCAS9+pMSPACER bla.A203G library+ pMTARGET-TEM1
B: MG1655+pMDCAS9+pMSPACER bla.A203G library+ pMTARGET-TEM1
C: MG1655+pMCAS9+pMSPACER bla.A203G library+ pMTARGET-TEM1-S68N
D: MG1655+pMDCAS9+pMSPACER bla.A203G library+ pMTARGET-TEM1-S68N Following the initial transformation events, the cells were allowed to recover for 2 hours at 37 C and the full recoveries were plated to 150 mm LB-spect-gent-zeo plates (yielding an average of 10000 colonies per plate). The plates were scraped and each respective cell slurry was suspended in 500 ul of PBS, washed once, and then used as the input for a standard miniprep plasmid extraction (Qiagen #27106). The following primers were used to prepare Illumina libraries from the plasmids preps (using 10 ng of input plasmid DNA):

PBP107:
(SEQ ID NO: 11)
CTTTCCCTACACGACGCTCTTCCGATCTNNNNGTAGAGATTGACATCCCT
ATCAGTGATA

PBP110:
(SEQ ID NO: 12)
GGAGTTCAGACGTGTGCTCTTCCGATCTAGACGTTCCCGTTGAATATGGC
TCATA

The resulting sequence data was analyzed using a custom pipeline to extract spacer sequences. For each of the targets (pMTARGET-TEM1 and pMTARGET-TEM1-S68N), the fold enrichment of each respective spacer, k, was generally calculated as follows:

$$E_k = \frac{\left(\frac{\text{Number of reads harboring spacer } k \text{ under } pMCAS9 \text{ condition}}{\text{Total number of reads for all spacers under } pMCAS9 \text{ condition}}\right)}{\left(\frac{\text{Number of reads harboring spacer } k \text{ under } pMDCAS9 \text{ condition}}{\text{Total number of reads for all spacers under } pMDCAS9 \text{ condition}}\right)}$$

This calculation can be thought of more simply as:

$$E_k = \frac{\text{Fractional representation of spacer } k \text{ under } pMCAS9 \text{ condition}}{\text{Fractional representation of spacer } k \text{ under } pMDCAS9 \text{ condition}}$$

For example, for determining the relative enrichment of spacer k in the presence of the wild type TEM-1 target, the following calculation (using the strain/condition lettering from above) is performed:

$$\frac{\text{Fractional representation of spacer } k \text{ under condition } A}{\text{Fractional representation of spacer } k \text{ under condition } B}$$

If the resulting relative enrichment is <1, then spacer k exhibits a measurable level of activity against the TEM-1 target. If the enrichment is >=1, then spacer k does not exhibit a measureable level of activity against the TEM-1 target.

Figure 6A:
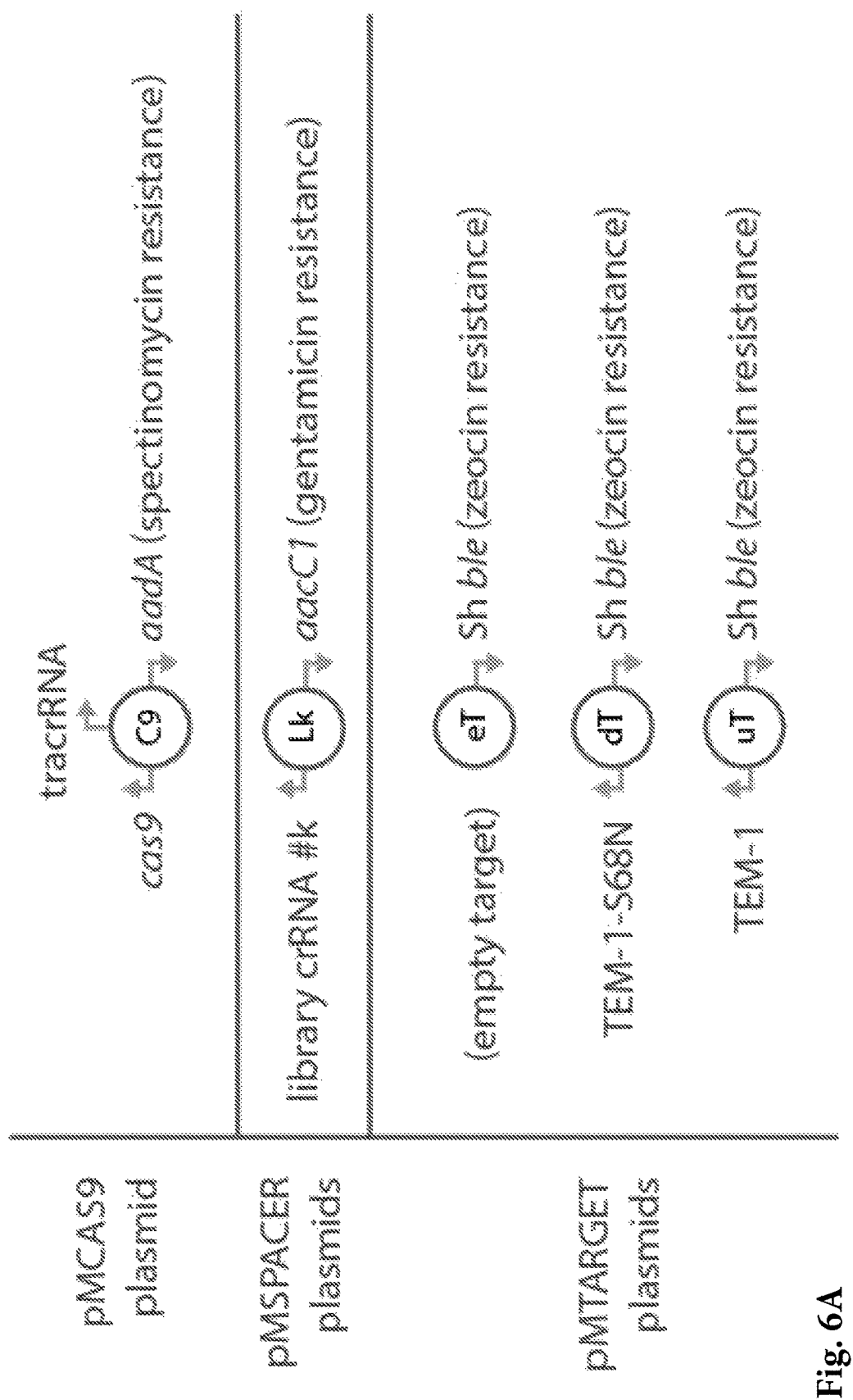
Figure 6B:
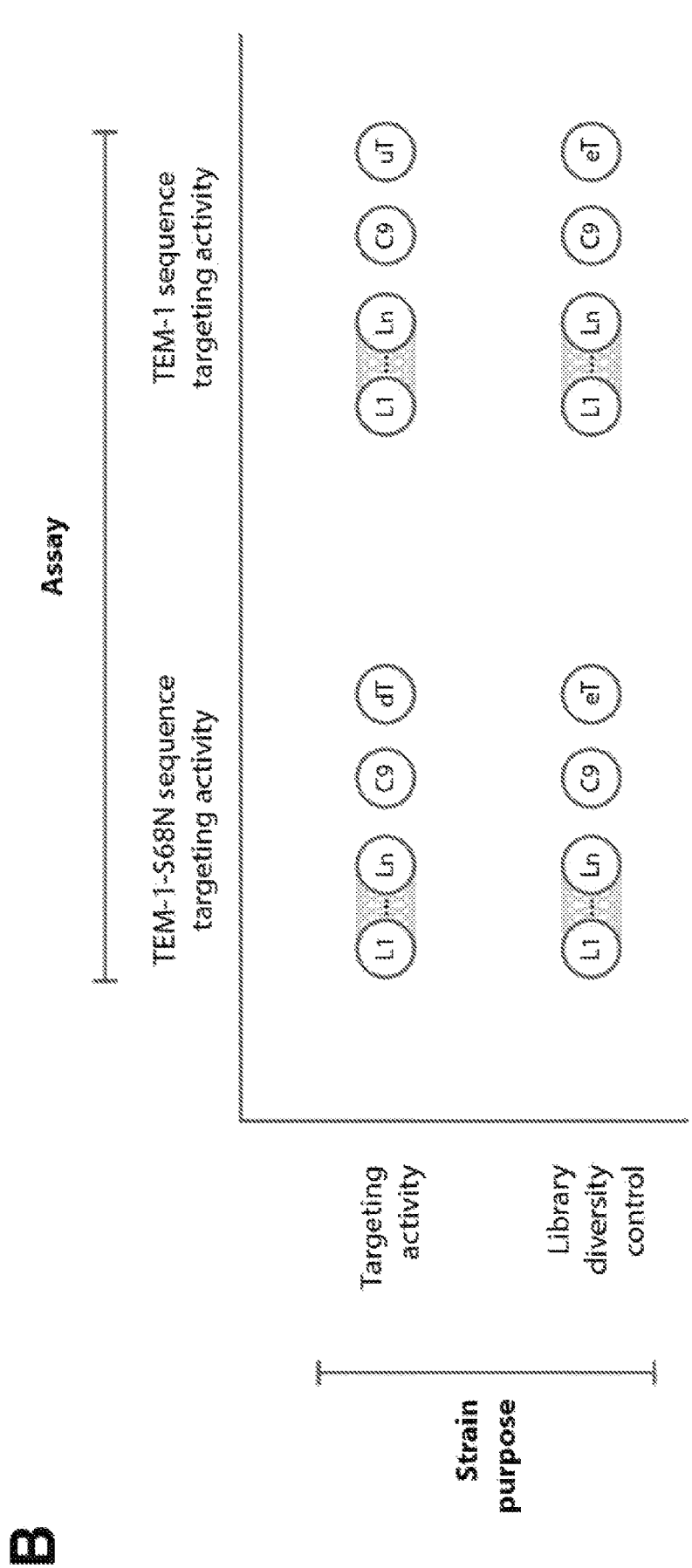
Figure 6G:
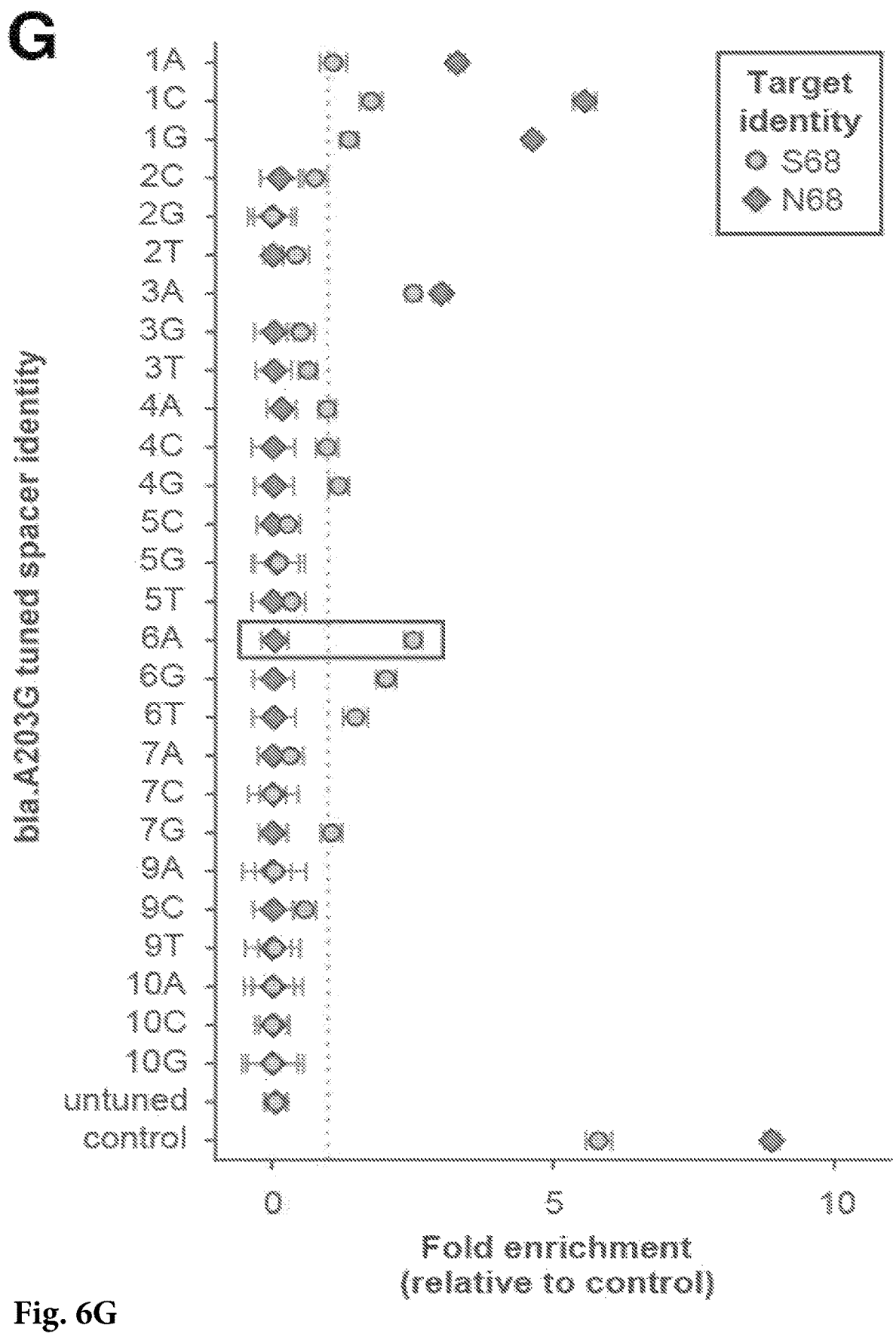
Figure 6H:
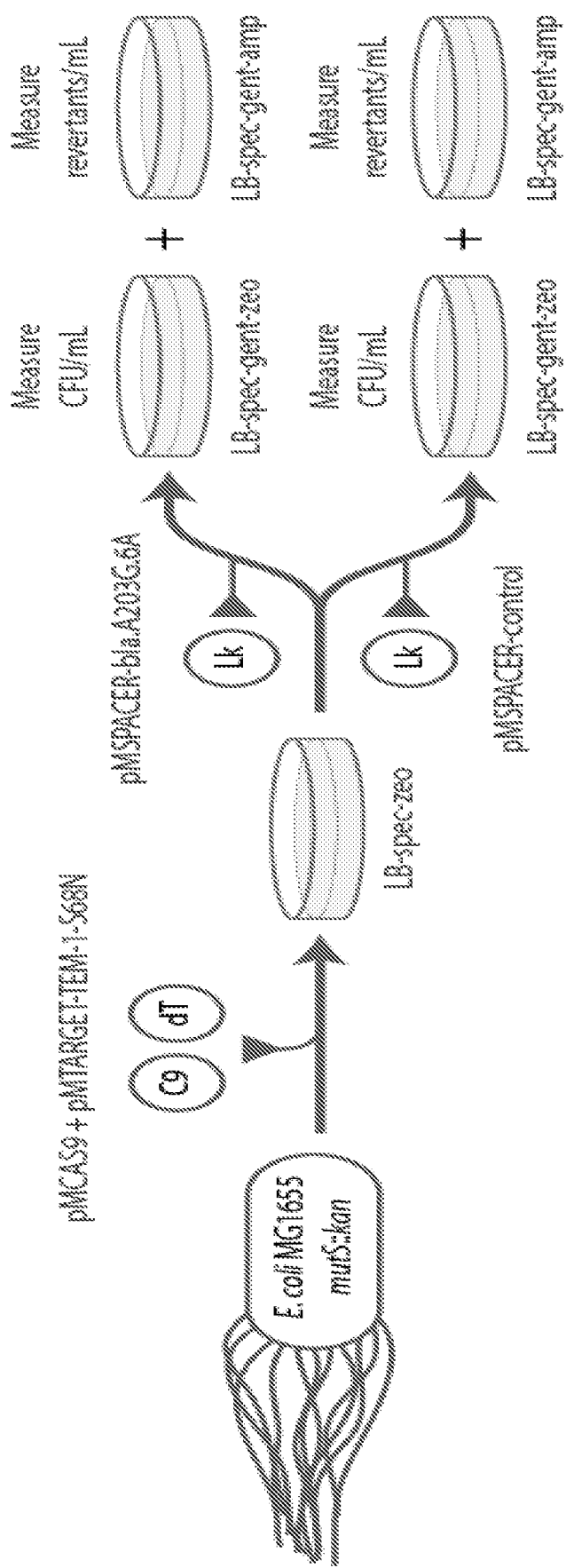
Figure 6I:
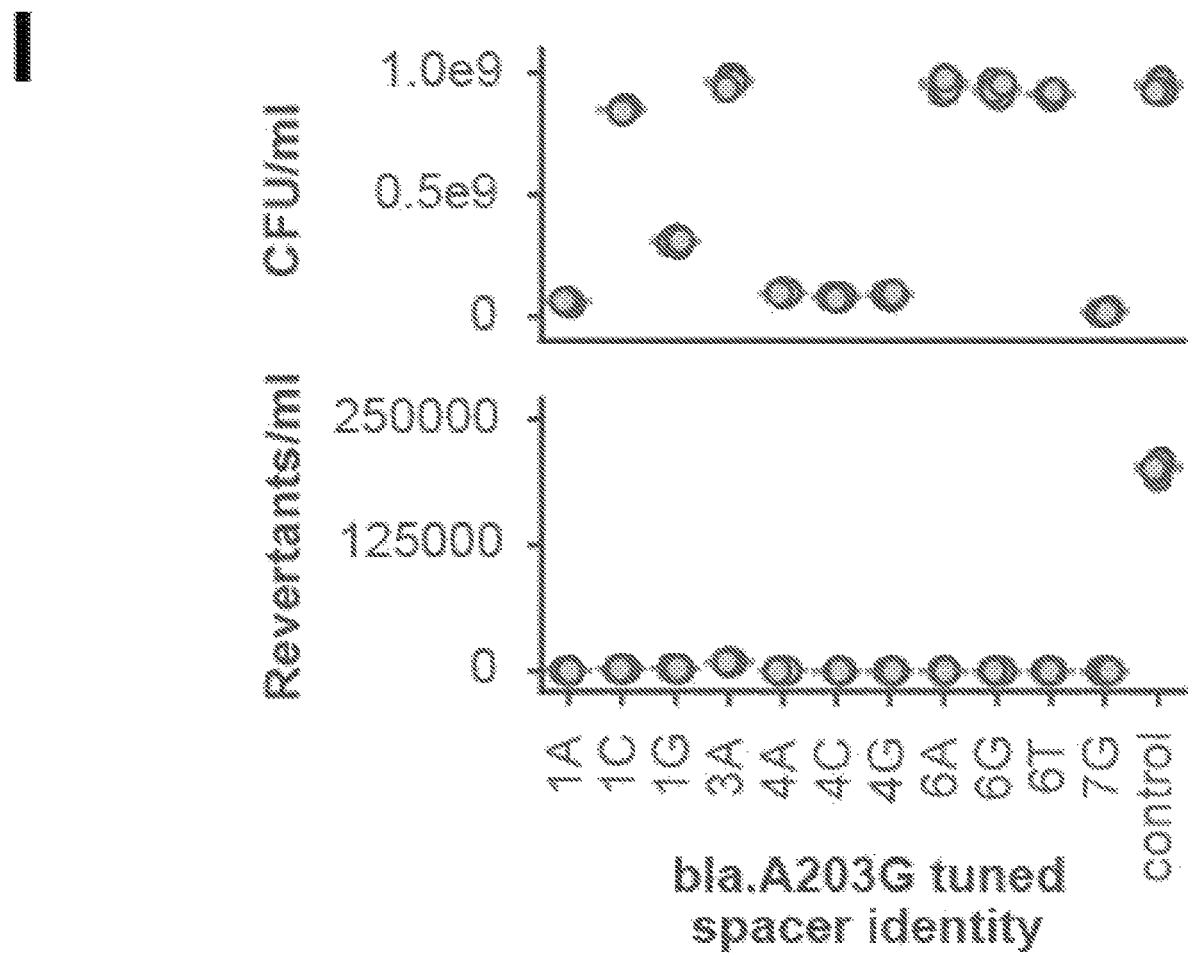

FIG. 6A and FIG. 6B depict the plasmids used during the bla.A203G spacer screening process. Each experimental strain contains a Cas9 plasmid (pMCAS9), the bla.A203G spacer library plasmids (pMSPACER-GG derivatives), and the appropriate target sequence plasmid (expressing TEM-1 or TEM-1-S68N, or the empty vector). FIG. 6C depicts that the screening process for activity against TEM-1/TEM-1-S68N proceeds as described in "Spacer library screen." FIGS. 6D-6F depict calculation workflow culminating in relative fold enrichment for bla.A203G.6A. In FIG. 6D, Illumina sequencing of the samples yields reads that can be mapped to the spacer library members. In FIG. 6E, the fraction of reads attributed to a given spacer (in this case, bla.A203G.6A) is calculated by dividing the number of reads attributed to the respective spacer by the total number of reads attributed to the sample. In FIG. 6F, the relative fold enrichment is calculated by normalizing the average read fraction by the average read fraction for the same spacer (bla.A204G.6A) from the library diversity control samples. In FIG. 6G, the resulting relative enrichment data is used to select spacer candidates that exhibit a high level of activity against the undesired sequence (in this case, wild type TEM-1 [S68S]) and minimal-to-no activity against the desired sequence (in this case, inactive TEM-1 [S68N]). in FIG. 6H, spacer candidates that exhibit high discriminatory power are subjected to confirmatory testing. In the case of TEM-1, spacers are assessed for their ability to prevent reversion of TEM-1-S68N to wild type, functionally-active TEM-1 (which confers resistance to ampicillin). A mutS-knockout strain is used to increase the stringency of the assay by artificially increasing mutation rates. In FIG. 6I, candidate spacers that do not confer a decrease in CFU/mL but do prevent reversions are those that have high discriminatory power. In this case, bla.A203G.6A has the greatest discriminatory power.

Figure 7A:
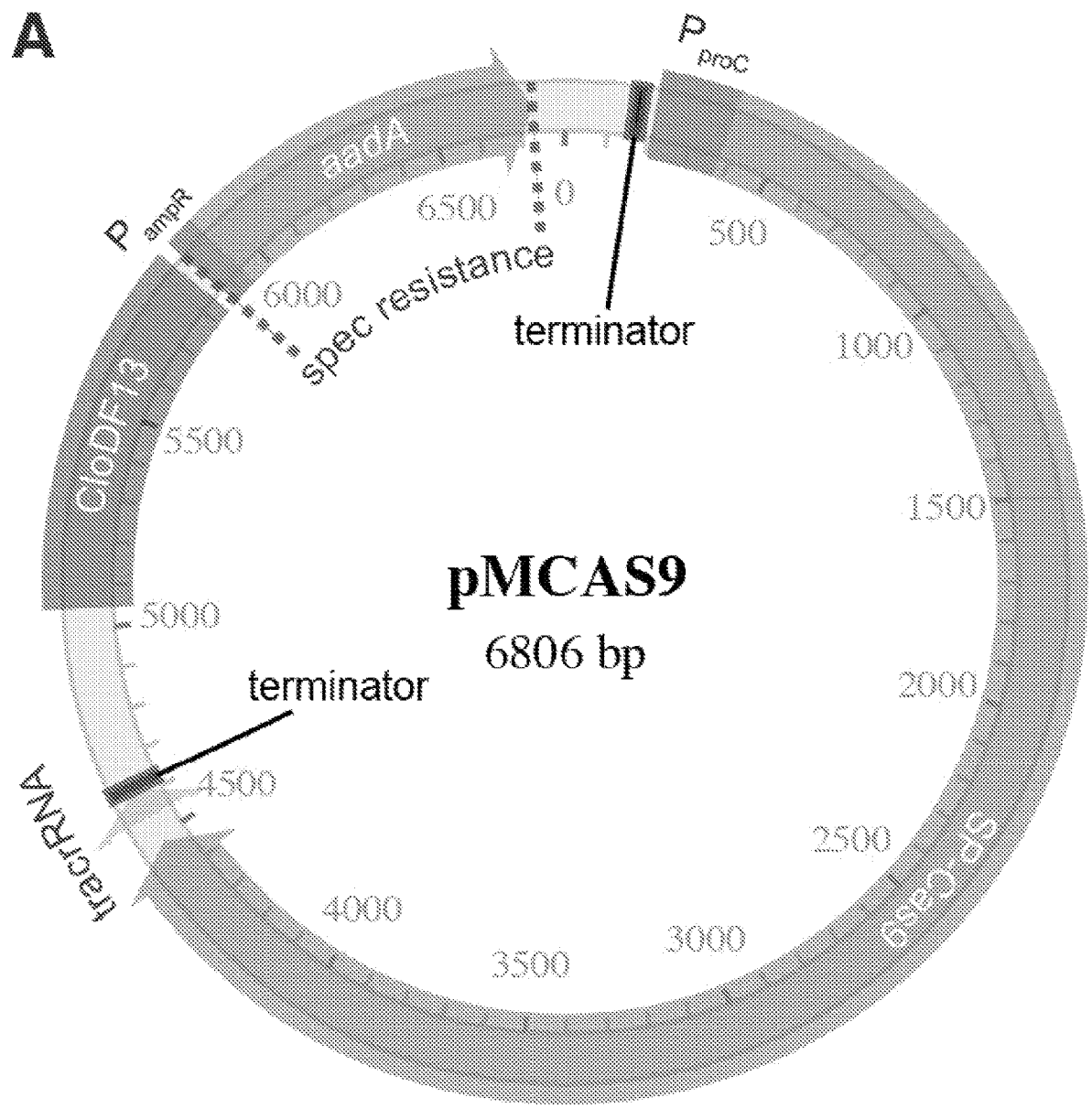
FIG. 7 depict exemplary plasmid systems.
Figure 7B:
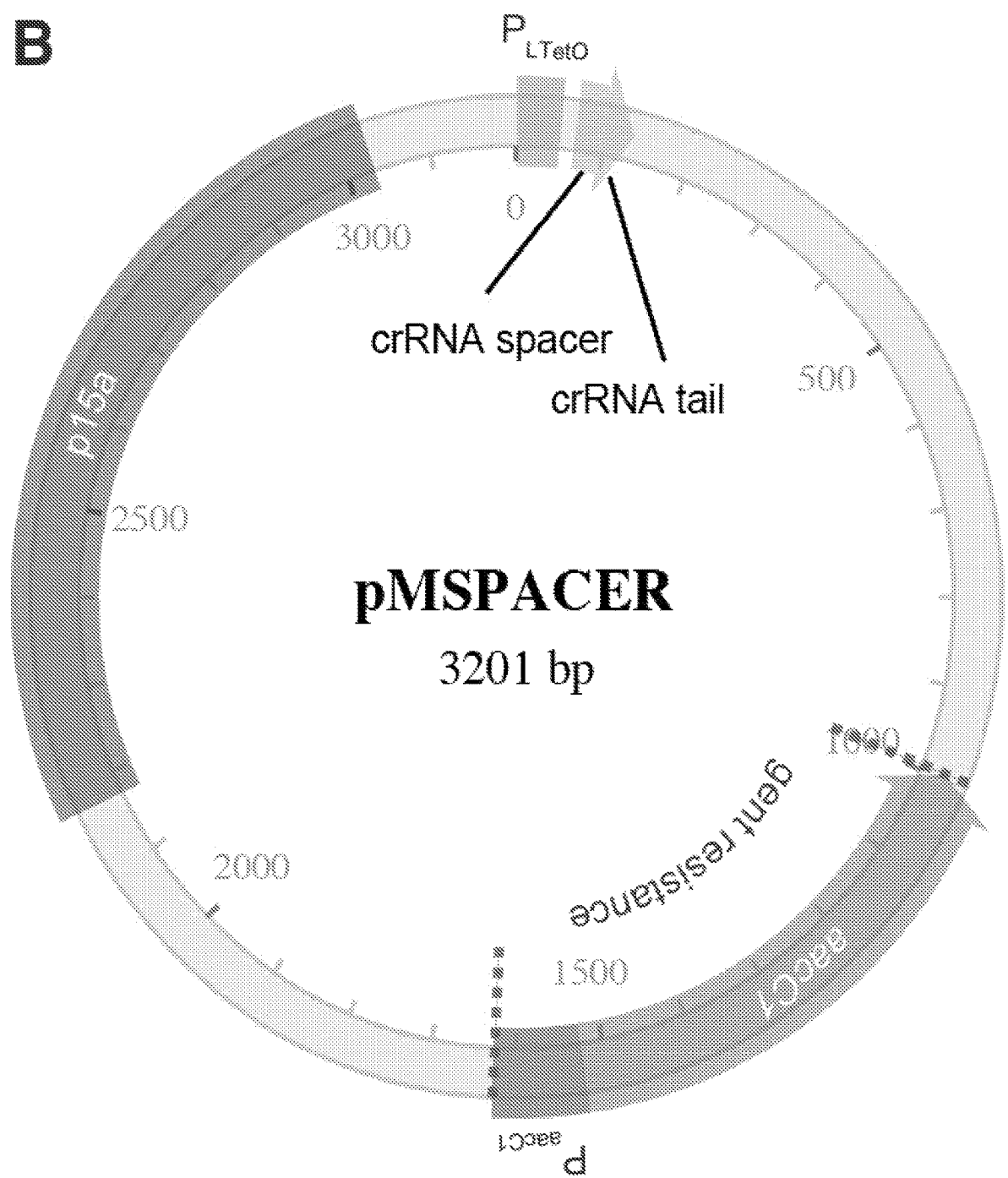
Figure 7C:
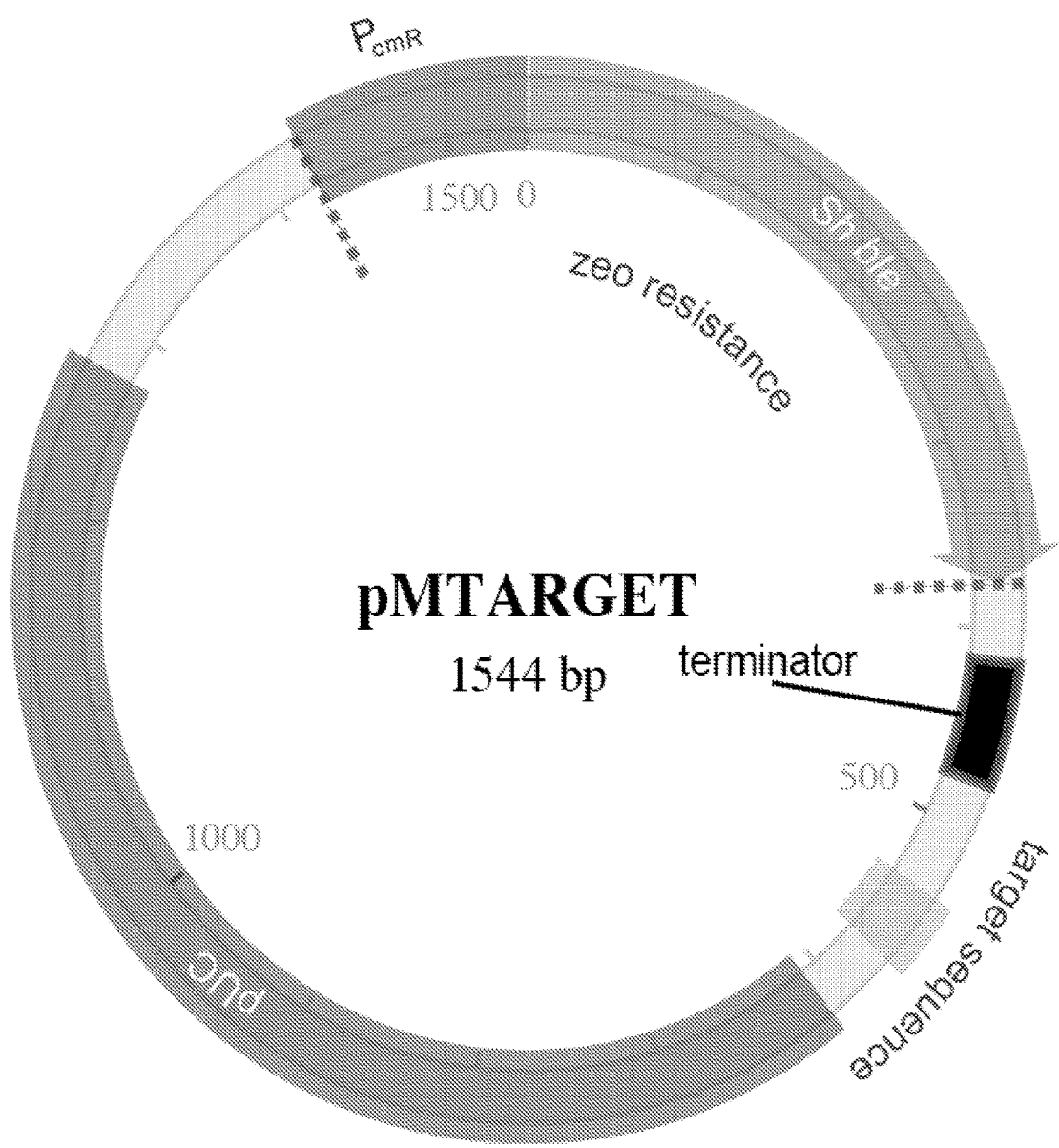

FIG. 7 depicts primary plasmid systems. The three primary plasmids backbones from which nearly all plasmids in this study are derived are pMCAS9, pMSPACER, and pMTARGET (FIG. 7A, FIG. 7B, FIG. 7C, respectively). Notable derivatives include pMDCAS9, in which the SP-Cas9 gene on pMCAS9 has been modified with the canonical D10A and H840A mutations to abrogate nuclease activity, as well as the golden gate cloning compatible versions of pMSPACER and pMTARGET (pMSPACER-GG and pMTARGET-GG).

Table 2 below shows bla.A203G spacer sequences used in the bla.A203G spacer screen.

| bla.A203G spacer identity | Sequence (5'-3') | Notes |
|---|---|---|
| 1A | ACATAGCAGAACTTTAAAAGTGCTCATCAa | (SEQ ID NO: 13) |
| 1G | ACATAGCAGAACTTTAAAAGTGCTCATCAg | (SEQ ID NO: 14) |
| 1C | ACATAGCAGAACTTTAAAAGTGCTCATCAc | (SEQ ID NO: 15) |
| 2T | ACATAGCAGAACTTTAAAAGTGCTCATCtT | (SEQ ID NO: 16) |
| 2G | ACATAGCAGAACTTTAAAAGTGCTCATCgT | (SEQ ID NO: 17) |
| 2C | ACATAGCAGAACTTTAAAAGTGCTCATCcT | (SEQ ID NO: 18) |
| 3A | ACATAGCAGAACTTTAAAAGTGCTCATaAT | (SEQ ID NO: 19) |
| 3T | ACATAGCAGAACTTTAAAAGTGCTCATtAT | (SEQ ID NO: 20) |
| 3G | ACATAGCAGAACTTTAAAAGTGCTCATgAT | (SEQ ID NO: 21) |
| 4A | ACATAGCAGAACTTTAAAAGTGCTCAaCAT | (SEQ ID NO: 22) |
| 4G | ACATAGCAGAACTTTAAAAGTGCTCAgCAT | (SEQ ID NO: 23) |
| 4C | ACATAGCAGAACTTTAAAAGTGCTCAcCAT | (SEQ ID NO: 24) |
| 5T | ACATAGCAGAACTTTAAAAGTGCTCtTCAT | (SEQ ID NO: 25) |
| 5G | ACATAGCAGAACTTTAAAAGTGCTCgTCAT | (SEQ ID NO: 26) |
| 5C | ACATAGCAGAACTTTAAAAGTGCTCcTCAT | (SEQ ID NO: 27) |
| 6A | ACATAGCAGAACTTTAAAAGTGCTaATCAT | (SEQ ID NO: 28) |
| 6T | ACATAGCAGAACTTTAAAAGTGCTtATCAT | (SEQ ID NO: 29) |
| 6G | ACATAGCAGAACTTTAAAAGTGCTgATCAT | (SEQ ID NO: 30) |
| 7A | ACATAGCAGAACTTTAAAAGTGCaCATCAT | (SEQ ID NO: 31) |
| 7G | ACATAGCAGAACTTTAAAAGTGCgCATCAT | (SEQ ID NO: 32) |
| 7C | ACATAGCAGAACTTTAAAAGTGCcCATCAT | (SEQ ID NO: 33) |
| 9A | ACATAGCAGAACTTTAAAAGTaCTCATCAT | (SEQ ID NO: 34) |
| 9T | ACATAGCAGAACTTTAAAAGTtCTCATCAT | (SEQ ID NO: 35) |
| 9C | ACATAGCAGAACTTTAAAAGTcCTCATCAT | (SEQ ID NO: 36) |
| 10A | ACATAGCAGAACTTTAAAAGaGCTCATCAT | (SEQ ID NO: 37) |
| 10G | ACATAGCAGAACTTTAAAAGgGCTCATCAT | (SEQ ID NO: 38) |
| 10C | ACATAGCAGAACTTTAAAAGcGCTCATCAT | (SEQ ID NO: 39) |
| untuned | ACATAGCAGAACTTTAAAAGTGCTCATCAT | (SEQ ID NO: 40) |
| control | ACTACAAGACACGTGCTGAAGTCAAGTTTG | Targets pBC-GFP (SEQ ID NO: 41) |

The naming convention is <base position from PAM/3' end><substituted base> (for example, 2 C refers to the spacer variant in which the $2^{nd}$ base from the 3' end is substituted for a cytosine). The substituted base is lowercase in the provided sequences. Note that the mutation being targeted (A203G) corresponds to the $8^{th}$ base from the 3' end of the spacer (which is why position 8 is invariant within the library). The control spacer is a functional spacer that cuts the pBC-GFP plasmid, but does not have any activity against the *E. coli* genome or any other study plasmids.

Example IV

Mutation Prevention

Figure 5:
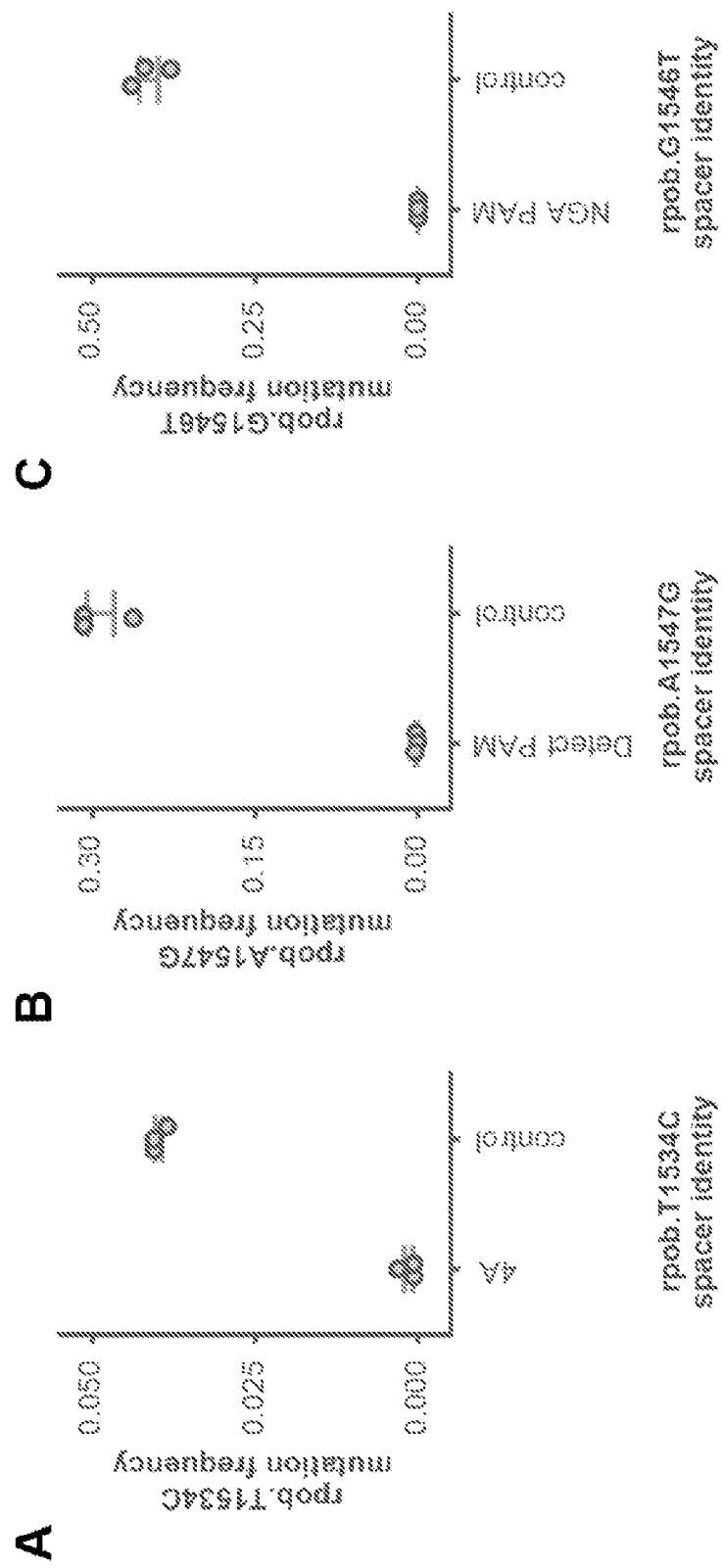
FIG. 5 depicts data of mutation frequency versus spacer identity.

A Cas9 guide RNA system using a tuned guide RNA is used to effectively prevent endogenous mutations that confers rifampicin resistance. See data in FIG. 5A. The mutation conferring rifampicin resistance actually creates a PAM sequence, which can be exploited to produce near-perfect discrimination (i.e., in the absence of the mutation, there is no NGG PAM sequence, so Cas9 will not bind at the target site, much less cut). See data in FIG. 5B. SP-Cas9 can be tuned to change its PAM specificity from NGG to NGA. The VQR variant of SP-Cas9 (with NGA PAM specificity) can be used to prevent a rifampicin resistance-conferring mutation that is proximal to an NGA PAM (but otherwise inaccessible to non-engineered SP-Cas9). See data in FIG. 5C. (In all cases n=3 and error bars are SEM).

Table 2 shows the spacer sequences used to demonstrate the portability of the mutation prevention system, single nucleotide discrimination across targeting principles (e.g., PAM creation detection) and Cas9 variants or orthologs (e.g., SP-Cas9-VQR, NM-Cas9, ST1-Cas9). Additional substitutions introduced through a tuning process are indicated in the spacer name and as a lower case letter in the spacer sequence. Spacers that require a non-canonical (non-NGG) PAM have names that are prefixed with the abbreviation for the respective Cas9 variant or ortholog.

control spacer for these experiments is the "empty" pMTARGET vector (without a spacer insert).

Experiments involving SP-Cas9 variants employed the SP-Cas9 D1135V/R1335Q/T1337R variant from Kleinstiver et al. 2015, hereon referred to as Cas9-VQR. The Cas9-VQR variant has an altered PAM specificity of NGA. Using this altered specificity, Cas9-VQR was tuned to prevent a G1546T mutation that confers rifampicin resistance by taking advantage of a nearby NGA spacer near the site of G1546T mutation (spacer sequences listed in Table 2). Aside from employing the Cas9-VQR variant and a unique spacer, all other aspects of the experimental workflow to quantify tuned spacer efficiency remained similar to those previously performed with wildtype SP-Cas9. For experiments involving NM-Cas9 and ST1-Cas9, the pMTARGET-TEM1-S68N plasmid was altered to include an NM (GTTA) or ST1 (GGAA) PAM downstream of the S68N mutation, thus enabling NM or ST1 Cas9 to target the S68S revertant. Due to cutting against the desired sequence (S68N) by untuned NM and ST1 spacers, a screen was performed to identify a tuned set of spacers for both NM and ST1 Cas9 that enabled each to selectively target the S68S TEM-1 allele (undesired target) while not appreciably affecting the S68N allele (desired target). The screening for these tuned spacers was identical to that for SP-Cas9 except the above mentioned mutations to endow the TEM-1 allele with the appropriate NM or ST1 PAM was employed during the screening and validation process. NM and ST1 Cas9 proteins and guide RNA expression plasmid have been previously described (Esvelt et al. 2013).

Example V

Applications

Aspects of the present methods are directed to the prevention of somatic and exogenous mutations in both prokaryotic and eukaryotic model systems. Such methods have particular application in academic study (e.g., understanding

| Spacer identity | Sequence (5'-3') | Notes |
|---|---|---|
| rpoB.T1534C.4A | GGGTTGTTCTGGTCCATAAACTGAGGaAGC | (SEQ ID NO: 42-47) |
| VQR-rpoB.G1546C | GTTCCAGCCAGCTGTCTCAGTTTATGAACC | NGA PAM (use VQR variant of SP-Cas9) |
| rpoB.A1547G | CTTCGGTTCCAGCCAGCTGTCTCAGTTTAT | Mutation creates NGG PAM |
| NM-bla.A203G.5G | TCGCCCCGAAGAACGTTTTCCAATGgTGAG | NM-Cas9 PAM |
| ST1-bla.A203G.3T | CCCCGAAGAACGTTTTCCAATGATGAGtAC | ST1-Cas9 PAM |
| pBC-GFP-2 | ACTACAAGACACGTGCTGAAGTCAAGTTTG | Targets pBC-GFP |

Figure 8:
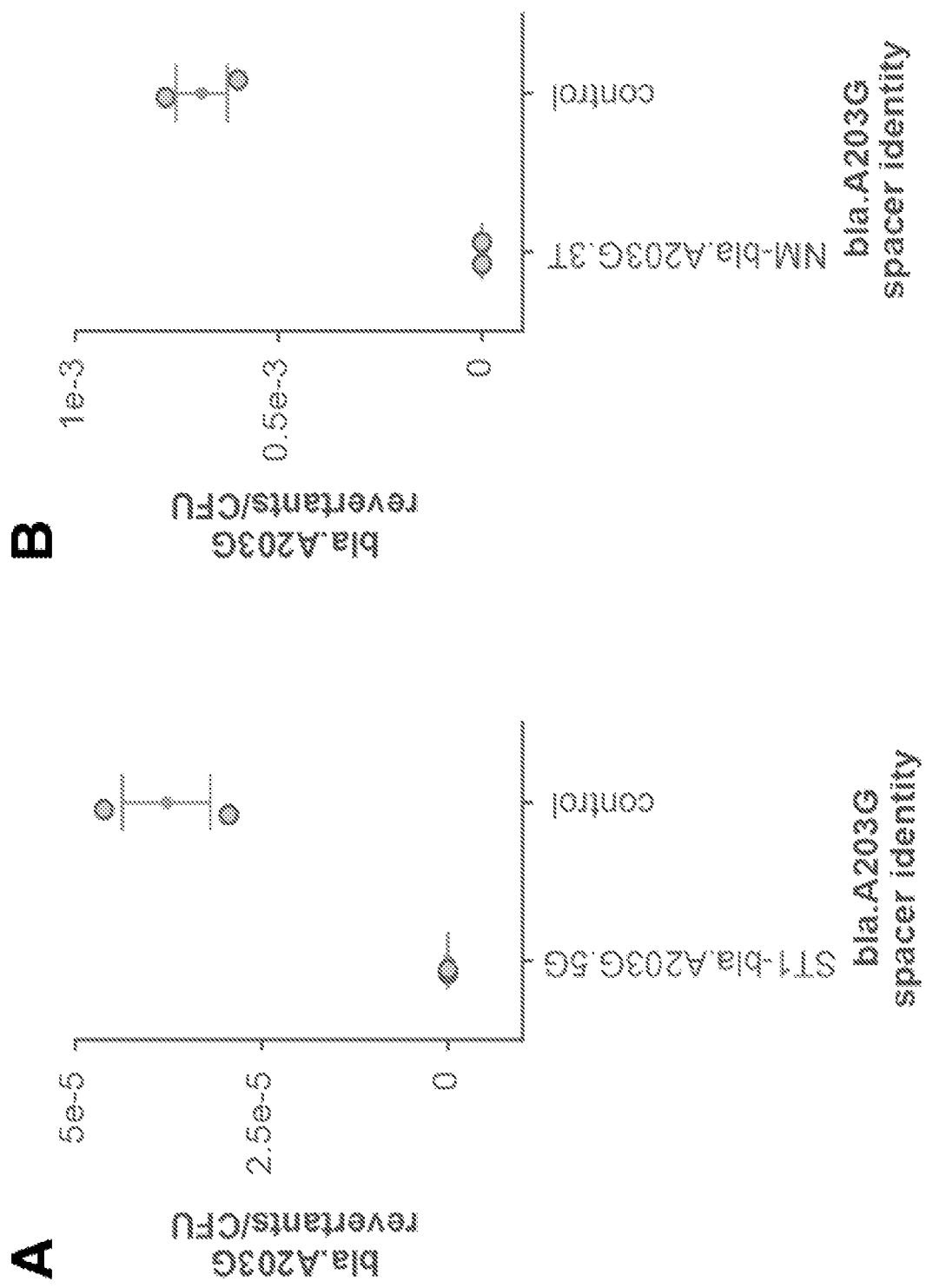
FIG. 8A-B depict data directed to Cas9 ortholog mutation prevention.

FIG. 8 includes data directed to Cas9 ortholog mutation prevention. The reversion of TEM-1-S68N is prevented using two different Cas9 orthologs, ST1-Cas9 (FIG. 8A) and NM-Cas9 (FIG. 8B). This demonstrates that the spacer tuning and mutation prevention principles that apply to SP-Cas9 are universally portable across orthologous Cas9 proteins and other nucleic acid-guided enzymes. The introduction of additional mismatches in the spacer sequence is an effective strategy to increase the discriminatory power of spacers used in conjunction with ST1-Cas9 and NM-Cas9. Moreover, these tuned spacers are able to prevent the occurrence of the TEM-1-S68N reversion mutation at equivalent (if not greater) efficiency to that of SP-Cas9. The multi-drug resistance); in metabolic engineering (e.g., preventing local maxima or minima during directed evolution experiments); in biosecurity (e.g., enforcing sequence integrity in barcode or potentially pathogenic regions) and in mutation prophylaxis in engineered organisms (e.g., preventing harmful mutations in engineered crops). Applications directed to a Cas/tuned guide RNA system that can discriminate between two protospacers that differ by one nucleotide include engineered cell lines and engineered organisms; targeted editing of dominant or recessive allele); Stem cell engineering (e.g., allele-specific targeting with SNP discrimination for expression perturbation; General gene expression perturbation; and Cas9-based labeling/imaging technologies. Further applications include stem cell engineering, disease modeling and engineered in vivo somatic/germline mutations, where the targeting of a mutant dominant allele or a particular paralogue of interest over other similar loci is desirable to ensure that only the given target gene is cut, thus stimulating its disruption or in the cases where a donor template is provided a method to alter the sequence of a particular single nucleotide variant. Additional and particular applications of the methods of using a tuned guide RNA described herein will be apparent to those of skill in the art based on the present disclosure.

Example VI

Embodiments

Aspects of the present disclosure are directed to a method of altering a target nucleic acid in a cell including providing to the cell a guide RNA having a spacer sequence that differs from a target protospacer sequence of same length by one or two or three nucleotides, wherein the target protospacer sequence is adjacent a PAM sequence, and wherein the target protospacer sequence differs from a nontarget sequence of same length by one or two nucleotides, providing to the cell a Cas9 protein or ortholog thereof, wherein the guide RNA spacer sequence binds to the target complementary protospacer sequence and the Cas9 protein or ortholog thereof interacts with the guide RNA to form a co-localization complex with the target nucleic acid and the target nucleic acid is cleaved in a site specific manner According to one aspect, the target protospacer sequence is a single point mutation of the nontarget sequence. According to one aspect, the target protospacer sequence is endogenous to the cell or exogenous to the cell. According to one aspect, the nontarget sequence is endogenous to the cell or exogenous to the cell. According to one aspect, cleaving of the target nucleic acid results in cell death. According to one aspect, the guide RNA spacer sequence discriminates between the target protospacer sequence and the nontarget sequence. According to one aspect, the guide RNA spacer sequence and the nontarget sequence are nonbinding. According to one aspect, the Cas9 protein or ortholog thereof is a Cas9 enzyme, a Cas9 nickase or a nuclease null Cas9 with a nuclease attached thereto. According to one aspect, the Cas9 protein is naturally occurring or engineered. According to one aspect, the cell is in vitro, in vivo or ex vivo. According to one aspect, the cell is a eukaryotic cell or a prokaryotic cell. According to one aspect, the cell is a bacteria cell, a yeast cell, a fungal cell, a mammalian cell, a human cell, a stem cell, a progenitor cell, an induced pluripotent stem cell, a human induced pluripotent stem cell, a plant cell or an animal cell. According to one aspect, the target nucleic acid is genomic DNA, mitochondrial DNA, plastid DNA, viral DNA, or exogenous DNA. According to one aspect, the one or two nucleotide difference is proximal to the PAM sequence. According to one aspect, the method further includes providing the cell with a donor nucleic acid, wherein the donor nucleic acid is inserted into the target nucleic acid. According to one aspect, the method further includes providing to the cell a plurality of guide RNAs each having a corresponding spacer sequence that differs from a target protospacer sequence of same length by one or two or three nucleotides, wherein the target protospacer sequence is adjacent a PAM sequence of a target nucleic acid, and wherein the target protospacer sequence differs from a nontarget sequence of same length by one or two nucleotides, providing to the cell a Cas9 protein or ortholog thereof, wherein the plurality of guide RNA spacer sequences bind to the corresponding target protospacer sequences and the Cas9 protein or ortholog thereof interacts with each of the plurality of guide RNAs to form co-localization complexes with target nucleic acids and the target nucleic acids are cleaved in a site specific manner According to one aspect, the guide RNA is provided to the cell by introducing into the cell a first foreign nucleic acid encoding the guide RNA. According to one aspect, the Cas9 is provided to the cell by introducing into the cell a second nucleic acid encoding the Cas9. According to one aspect, the guide RNA is provided to the cell by introducing into the cell a first foreign nucleic acid encoding the guide RNA within a vector and wherein the Cas9 is provided to the cell by introducing into the cell a second nucleic acid encoding the Cas9 within a vector, and wherein the first foreign nucleic acid and the second foreign nucleic acid are provided on the same or different vectors. According to one aspect, the guide RNA is provided to the cell as a native guide RNA. According to one aspect, the Cas9 is provided to the cell as a native species.

According to certain embodiments, a method of genetically modifying a cell to include a genome editing system which targets single point mutations in cell progeny for target nucleic acid cleavage is provided including providing to the cell a first nucleic acid encoding a guide RNA having a spacer sequence that differs from a target protospacer sequence of same length by one or two nucleotides, wherein the target protospacer sequence is a single point mutation of the nontarget sequence, providing to the cell a second nucleic acid encoding a Cas9 protein, providing the cell under conditions where first cell progeny is produced including the target protospacer sequence and second cell progeny is produced including the nontarget sequence, wherein the guide RNA spacer sequence binds to the target protospacer sequence and the Cas9 protein interacts with the guide RNA to form a co-localization complex with the target nucleic acid and the target nucleic acid is cleaved in a site specific manner. According to one aspect, cleaving of the target nucleic acid results in cell death. According to one aspect, the guide RNA spacer sequence and the nontarget sequence of the second cell progeny are nonbinding. According to one aspect, the Cas9 protein is a Cas9 enzyme, a Cas9 nickase or a nuclease null Cas9 protein with a nuclease attached thereto. According to one aspect, the cell is in vitro, in vivo or ex vivo. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, an induced pluripotent stem cell, a human induced pluripotent stem cell, a plant cell or an animal cell. According to one aspect, the target nucleic acid is genomic DNA, mitochondrial DNA, plastid DNA, viral DNA, or exogenous DNA. According to one aspect, the one or two nucleotide difference is proximal to the PAM sequence.

According to certain embodiments, a cell is provided including a guide RNA having a spacer sequence that differs from a target protospacer sequence of same length by one or two nucleotides, wherein the target protospacer sequence is adjacent a PAM sequence, and wherein the target protospacer sequence differs from a nontarget sequence of same length by one nucleotide, and a Cas9 protein or ortholog thereof, wherein the guide RNA and the Cas9 protein or ortholog thereof are members of a co-localization complex for a target nucleic acid. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, an induced pluripotent stem cell, a human induced pluripotent stem cell, a plant cell or an animal cell.

According to certain embodiments, a cell is provided including a first nucleic acid encoding a guide RNA having a spacer sequence that differs from a target protospacer sequence of same length by one or two nucleotides, wherein the target protospacer sequence is adjacent a PAM sequence, and wherein the target protospacer sequence differs from a nontarget sequence of same length by one nucleotide, and a second nucleic acid encoding a Cas9 protein or ortholog thereof, wherein the guide RNA and the Cas9 protein or ortholog thereof are members of a co-localization complex for a target nucleic acid. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, an induced pluripotent stem cell, a human induced pluripotent stem cell, a plant cell or an animal cell. According to one aspect, an organism is provided that includes one or more of the cells described herein.

According to certain embodiments, a method of altering a target nucleic acid in a cell is provided including providing to the cell a guide RNA having a spacer sequence entirely complementary to a target protospacer sequence of same length except for a one or two nucleotide mismatch with the target protospacer sequence, wherein the target protospacer sequence is adjacent a PAM sequence, and wherein the target protospacer sequence differs from a nontarget sequence of same length by one nucleotide, providing to the cell a Cas9 protein or ortholog thereof, wherein the guide RNA spacer sequence binds to the target protospacer sequence and the Cas9 protein or ortholog thereof interacts with the guide RNA to form a co-localization complex with the target nucleic acid and the target nucleic acid is cleaved in a site specific manner.

According to certain embodiments, a method of genetically modifying a cell to include a genome editing system which targets single point mutations in cell progeny for target nucleic acid cleavage is provided including providing to the cell a first nucleic acid encoding a guide RNA having a spacer sequence entirely complementary to a target protospacer sequence except for a one or two nucleotide mismatch with the target protospacer sequence, wherein the target protospacer sequence is a single point mutation of the nontarget sequence, providing to the cell a second nucleic acid encoding a Cas9 protein, providing the cell under conditions where first cell progeny is produced including the target protospacer sequence and second cell progeny is produced including the nontarget sequence, wherein the guide RNA spacer sequence binds to the target protospacer sequence and the Cas9 protein interacts with the guide RNA to form a co-localization complex with the target nucleic acid and the target nucleic acid is cleaved in a site specific manner.

According to certain embodiments, a cell is provided including a guide RNA having a spacer sequence entirely complementary to a target protospacer sequence of same length except for a one or two nucleotide mismatch with the target protospacer sequence, wherein the target protospacer sequence is adjacent a PAM sequence, and wherein the target protospacer sequence differs from a nontarget sequence of same length by one nucleotide, and a Cas9 protein or ortholog thereof, wherein the guide RNA and the Cas9 protein or ortholog thereof are members of a co-localization complex for a target nucleic acid.

According to certain embodiments, a cell is provided including a first nucleic acid encoding a guide RNA having a spacer sequence entirely complementary to a target protospacer sequence of same length except for a one or two nucleotide mismatch with the target protospacer sequence, wherein the target protospacer sequence is adjacent a PAM sequence, and wherein the target protospacer sequence differs from a nontarget sequence of same length by one nucleotide, and a second nucleic acid encoding a Cas9 protein or ortholog thereof, wherein the guide RNA and the Cas9 protein or ortholog thereof are members of a co-localization complex for a target nucleic acid.

According to certain embodiments, a method of identifying one or more discriminatory guide RNA from a library of guide RNA that discriminate between a target protospacer sequence that differs from a nontarget sequence of same length by one nucleotide wherein the library of guide RNA have a spacer sequence entirely complementary to the target protospacer sequence of same length except for a one or two nucleotide mismatch with the target protospacer sequence is provided including (a) combining the library of guide RNA with a strain including the nontarget sequence and a Cas9 enzyme and determining cutting rate of candidate guide RNA for the nontarget sequence, (b) combining the library of guide RNA with a strain including the nontarget sequence, a Cas9 enzyme and a plasmid including the target protospacer sequence and determining cutting rate of candidate guide RNA for the target protospacer sequence, (c) normalizing the cutting rates of step (a) and step (b) wherein guide RNA having a high cutting rate of the target protospacer sequence and a low cutting rate of the nontarget sequence are discriminatory guide RNA.

According to certain embodiments, a method of designing a guide RNA to discriminate between a target protospacer sequence and a nontarget sequence of same length wherein the target protospacer sequence differs from the nontarget sequence of same length by a first nucleotide is provided including designing the guide RNA to be exactly complementary to the target protospacer sequence except for a one or two nucleotide mismatch with the target protospacer sequence.

According to certain embodiments, a method of designing a guide RNA to discriminate between a target protospacer sequence and a nontarget sequence of same length wherein the target protospacer sequence differs from the nontarget sequence of same length by a first nucleotide is provided including designing the guide RNA to differ from the target protospacer sequence by one or two nucleotides.

According to certain embodiments, a method of identifying one or more discriminatory guide RNA from a library of guide RNA that discriminate between a target protospacer sequence that differs from a nontarget sequence of same length by one nucleotide wherein the library of guide RNA have a spacer sequence that differs from a target protospacer sequence of same length by one or two nucleotides is provided including (a) combining the library of guide RNA with a strain including the nontarget sequence and a Cas9 enzyme and determining cutting rate of candidate guide RNA for the nontarget sequence, (b) combining the library of guide RNA with a strain including the nontarget sequence, a Cas9 enzyme and a plasmid including the target protospacer sequence and determining cutting rate of candidate guide RNA for the target protospacer sequence, (c) normalizing the cutting rates of step (a) and step (b) wherein guide RNA having a high cutting rate of the target protospacer sequence and a low cutting rate of the nontarget sequence are discriminatory guide RNA.

According to certain embodiments, a method of identifying one or more discriminatory guide RNA from a library of guide RNA that discriminate between a target protospacer sequence that differs from a nontarget sequence of same length by one nucleotide wherein the library of guide RNA have a spacer sequence entirely complementary to the target protospacer sequence of same length except for a one or two nucleotide mismatch with the target protospacer sequence is provided including (a) combining the library of guide RNA with a strain including a Cas9 enzyme and a plasmid including the nontarget sequence and determining cutting rate of candidate guide RNA for the nontarget sequence, (b) combining the library of guide RNA with a strain including Cas9 and a plasmid including the target protospacer sequence and determining cutting rate of candidate guide RNA for the target protospacer sequence, (c) normalizing the cutting rates of step (a) and step (b) wherein guide RNA having a high cutting rate of the target protospacer sequence and a low cutting rate of the nontarget sequence are discriminatory guide RNA.

According to certain embodiments, a method of identifying one or more discriminatory guide RNA from a library of guide RNA that discriminate between a target protospacer sequence that differs from a nontarget sequence of same length by one nucleotide wherein the library of guide RNA have a spacer sequence that differs from a target protospacer sequence of same length by one or two nucleotides is provided including (a) combining the library of guide RNA with a strain including a Cas9 enzyme and a plasmid including the nontarget sequence and determining cutting rate of candidate guide RNA for the nontarget sequence, (b) combining the library of guide RNA with a strain including Cas9 and a plasmid including the target protospacer sequence and determining cutting rate of candidate guide RNA for the target protospacer sequence, (c) normalizing the cutting rates of step (a) and step (b) wherein guide RNA having a high cutting rate of the target protospacer sequence and a low cutting rate of the nontarget sequence are discriminatory guide RNA.

The invention claimed is:

1. A method of discriminating for Cas9 cutting between a target protospacer sequence in a target nucleic acid and a non-target protospacer sequence of same length in a cell comprising
providing to the cell a guide RNA having a spacer sequence that is of same length and is entirely complementary to the target protospacer sequence except that it differs from the target protospacer sequence of same length by one or two or three nucleotides, wherein the target protospacer sequence is adjacent to a PAM sequence and the one or two or three nucleotide difference is proximal to the PAM sequence, and wherein the target protospacer sequence differs from the non-target protospacer sequence of same length by one or two nucleotides,
providing to the cell a Cas9 protein,
wherein the guide RNA spacer sequence discriminately binds to the target protospacer sequence versus the non-target protospacer sequence in the cell and the Cas9 protein interacts with the guide RNA to form a co-localization complex with the target nucleic acid and the target nucleic acid is cut or nicked in a site specific manner.

2. The method of claim 1 wherein the target protospacer sequence is a single point mutation of the non-target sequence.

3. The method of claim 1 wherein the target protospacer sequence is endogenous to the cell or exogenous to the cell.

4. The method of claim 1 wherein the non-target sequence is endogenous to the cell or exogenous to the cell.

5. The method of claim 1 wherein cleaving of the target nucleic acid results in cell death.

6. The method of claim 1 wherein the guide RNA spacer sequence and the non-target sequence are nonbinding.

7. The method of claim 1 wherein the Cas9 protein is a Cas9 enzyme, a Cas9 nickase or a nuclease null Cas9 with a nuclease attached thereto.

8. The method of claim 1 wherein the Cas9 protein is naturally occurring or engineered.

9. The method of claim 1 wherein the cell is in vitro, in vivo or ex vivo.

10. The method of claim 1 wherein the cell is a eukaryotic cell or a prokaryotic cell.

11. The method of claim 1 wherein the cell is a bacteria cell, a yeast cell, a fungal cell, a mammalian cell, a human cell, a stem cell, a progenitor cell, an induced pluripotent stem cell, a human induced pluripotent stem cell, a plant cell or an animal cell.

12. The method of claim 1 wherein the target nucleic acid is genomic DNA, mitochondrial DNA, plastid DNA, viral DNA, or exogenous DNA.

13. The method of claim 1 further comprising providing the cell with a donor nucleic acid, wherein the donor nucleic acid is inserted into the target nucleic acid.

14. The method of claim 1 further including
providing to the cell a plurality of guide RNAs each having a corresponding spacer sequence that differs from a target protospacer sequence of same length by one or two or three nucleotides, wherein the target protospacer sequence is adjacent a PAM sequence of a target nucleic acid, and wherein the target protospacer sequence differs from a non-target sequence of same length by one or two nucleotides,
providing to the cell a Cas9 protein,
wherein the plurality of guide RNA spacer sequences bind to the corresponding target protospacer sequences and the Cas9 protein interacts with each of the plurality of guide RNAs to form co-localization complexes with target nucleic acids and the target nucleic acids are cut or nicked in a site specific manner.

15. The method of claim 1 wherein the guide RNA is provided to the cell by introducing into the cell a first foreign nucleic acid encoding the guide RNA.

16. The method of claim 1 wherein the Cas9 is provided to the cell by introducing into the cell a second nucleic acid encoding the Cas9.

17. The method of claim 1 wherein the guide RNA is provided to the cell by introducing into the cell a first foreign nucleic acid encoding the guide RNA within a vector and wherein the Cas9 is provided to the cell by introducing into the cell a second nucleic acid encoding the Cas9 within a vector, and wherein the first foreign nucleic acid and the second foreign nucleic acid are provided on the same or different vectors.

18. The method of claim 1 wherein the guide RNA is provided to the cell as a native guide RNA.

19. The method of claim 1 wherein the Cas9 is provided to the cell as a native species.

20. The method of claim 1 wherein the spacer sequence is entirely complementary to a target protospacer sequence of same length except for a one or two nucleotide mismatch with the target protospacer sequence, wherein the target protospacer sequence is adjacent a PAM sequence, and wherein the target protospacer sequence differs from a nontarget sequence of same length by one nucleotide.

21. The method of claim 1 wherein the gRNA exhibits greater than 90% efficiency against the target protospacer sequence and less than 10% efficiency against the nontarget protospacer sequence.

22. The method of claim 1 wherein the one or two or three nucleotide difference is within 6 nucleotides of the PAM sequence.

23. A method of genetically modifying a cell to include a genome editing system which targets single point mutations in cell progeny for target nucleic acid cutting or nicking comprising
providing to the cell a first nucleic acid encoding a guide RNA having a spacer sequence that is entirely complementary to a target protospacer sequence of same length that is adjacent to a PAM sequence except for a one or two nucleotide mismatch with the target protospacer sequence and the one or two nucleotide mismatch is proximal to the PAM sequence, wherein the target protospacer sequence is present in the cell and wherein the target protospacer sequence is a single point mutation of a non-target protospacer sequence present in the cell, wherein the guide RNA spacer sequence discriminately binds to the target protospacer sequence versus the non-target protospacer sequence in the cell,
providing to the cell a second nucleic acid encoding a Cas9 protein,
providing the cell under conditions where a first cell progeny is produced including the target protospacer sequence and a second cell progeny is produced including the non-target sequence,
wherein the guide RNA spacer sequence binds to the target protospacer sequence and the Cas9 protein interacts with the guide RNA to form a co-localization complex with the target nucleic acid and the target nucleic acid is cut or nicked in a site specific manner.

24. An isolated cell comprising
a guide RNA having a spacer sequence that differs from a target protospacer sequence of same length by one or two nucleotides, wherein the target protospacer sequence is adjacent a PAM sequence, and wherein the target protospacer sequence differs from a non-target protospacer sequence of same length by one nucleotide, wherein the target protospacer sequence and the non-target protospacer sequence are present in the cell, and
a Cas9 protein, wherein the guide RNA and the Cas9 protein are members of a co-localization complex for a target nucleic acid,
wherein the guide RNA spacer sequence discriminately binds to the target protospacer sequence versus the non-target protospacer sequence and wherein the gRNA exhibits greater than 90% efficiency against the target protospacer sequence and less than 10% efficiency against the nontarget protospacer sequence.

25. An isolated cell comprising
a first nucleic acid encoding a guide RNA having a spacer sequence that differs from a target protospacer sequence of same length by one or two nucleotides, wherein the target protospacer sequence is adjacent a PAM sequence, and wherein the target protospacer sequence differs from a non-target protospacer sequence of same length by one nucleotide, wherein the target protospacer sequence and the non-target protospacer sequence are present in the cell, and
a second nucleic acid encoding a Cas9 protein, wherein the guide RNA and the Cas9 protein are members of a co-localization complex for a target nucleic acid,
wherein the guide RNA spacer sequence discriminately binds to the target protospacer sequence versus the non-target protospacer sequence and wherein the gRNA exhibits greater than 90% efficiency against the target protospacer sequence and less than 10% efficiency against the non-target protospacer sequence.

26. An isolated cell comprising
a first nucleic acid encoding a guide RNA having a spacer sequence entirely complementary to a target protospacer sequence of same length except for a one or two nucleotide mismatch with the target protospacer sequence, wherein the target protospacer sequence is adjacent a PAM sequence and the one or two mismatch is proximal to the PAM sequence, and wherein the target protospacer sequence differs from a non-target protospacer sequence of same length by one nucleotide, wherein the target protospacer sequence and the non-target protospacer sequence are present in the cell, and
a second nucleic acid encoding a Cas9 protein, wherein the guide RNA and the Cas9 protein are members of a co-localization complex for a target nucleic acid,
wherein the guide RNA spacer sequence discriminately binds to the target protospacer sequence versus the non-target protospacer sequence and wherein the gRNA exhibits greater than 90% efficiency against the target protospacer sequence and less than 10% efficiency against the non-target protospacer sequence.

27. A method of identifying one or more discriminatory guide RNA from a library of guide RNA that discriminate between a target protospacer sequence that is adjacent to a PAM sequence that differs from a non-target sequence of same length by one nucleotide wherein the library of guide RNA have a spacer sequence entirely complementary to the target protospacer sequence of same length except for a one or two nucleotide mismatch with the target protospacer sequence comprising (a)(i) providing an isolated cell comprising
a first nucleic acid encoding a guide RNA having a spacer sequence entirely complementary to a target protospacer sequence of same length except for a one or two nucleotide mismatch with the target protospacer sequence, wherein the target protospacer sequence is adjacent a PAM sequence and the one or two mismatch is proximal to the PAM sequence, and wherein the target protospacer sequence differs from a non-target protospacer sequence of same length by one nucleotide, and
a second nucleic acid encoding a Cas9 protein, wherein the guide RNA and the Cas9 protein are members of a co-localization complex for a target nucleic acid,
wherein the guide RNA spacer sequence discriminately binds to the target protospacer sequence versus the non-target protospacer sequence, (a) combining the library of guide RNA with a strain including the non-target sequence and a Cas9 enzyme and determining cutting rate of candidate guide RNA for the non-target sequence, (b) combining the library of guide RNA with a strain including the non-target sequence, a Cas9 enzyme and a plasmid including the target protospacer sequence and determining cutting rate of candidate guide RNA for the target protospacer sequence, (c) normalizing the cutting rates of step (a) and step (b) wherein guide RNA having a high cutting rate of the target protospacer sequence and a low cutting rate of the non-target sequence are discriminatory guide RNA, wherein a high cutting rate is greater than 90% efficiency and a low cutting rate is less than 10% efficiency.

* * * * *

SEQUENCE LISTING

<160> NUMBER OF SEQ ID NOS: 47

<210> SEQ ID NO 1
<211> LENGTH: 27
<212> TYPE: DNA
<213> ORGANISM: Artificial
<220> FEATURE:
<223> OTHER INFORMATION: spacer sequence

<400> SEQUENCE: 1
tagcagaact ttaaaagtgt tcatcat        27

<210> SEQ ID NO 2
<211> LENGTH: 30
<212> TYPE: DNA
<213> ORGANISM: Artificial
<220> FEATURE:
<223> OTHER INFORMATION: spacer sequence

<400> SEQUENCE: 2
tagcagaact ttaaaagtgt tcatcattgg        30

<210> SEQ ID NO 3
<211> LENGTH: 27
<212> TYPE: DNA
<213> ORGANISM: Artificial
<220> FEATURE:
<223> OTHER INFORMATION: spacer sequence

<400> SEQUENCE: 3
tagcagaact ttaaaagtgt tcatcat        27

<210> SEQ ID NO 4
<211> LENGTH: 83
<212> TYPE: DNA
<213> ORGANISM: Artificial
<220> FEATURE:
<223> OTHER INFORMATION: N20_8 tracr sequence

<400> SEQUENCE: 4
gttttagagc tagaaatagc aagttaaaat aaggctagtc cgttatcaac ttgaaaaagt        60
ggcaccgagt cggtgctttt ttt        83

-continued

```
<210> SEQ ID NO 5
<211> LENGTH: 1368
<212> TYPE: PRT
<213> ORGANISM: Streptococcus pyogenes

<400> SEQUENCE: 5
```

| | | | | | | | | | | | | | | | |
|---|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |
| Gly | Trp | Ala | Val | Ile | Thr | Asp | Glu | Tyr | Lys | Val | Pro | Ser | Lys | Lys | Phe |
| | | | 20 | | | | | 25 | | | | | 30 | | |
| Lys | Val | Leu | Gly | Asn | Thr | Asp | Arg | His | Ser | Ile | Lys | Lys | Asn | Leu | Ile |
| | | | 35 | | | | | 40 | | | | | 45 | | |
| Gly | Ala | Leu | Leu | Phe | Asp | Ser | Gly | Glu | Thr | Ala | Glu | Ala | Thr | Arg | Leu |
| | 50 | | | | | 55 | | | | | 60 | | | | |
| Lys | Arg | Thr | Ala | Arg | Arg | Arg | Tyr | Thr | Arg | Arg | Lys | Asn | Arg | Ile | Cys |
| 65 | | | | | 70 | | | | | 75 | | | | | 80 |
| Tyr | Leu | Gln | Glu | Ile | Phe | Ser | Asn | Glu | Met | Ala | Lys | Val | Asp | Asp | Ser |
| | | | | 85 | | | | | 90 | | | | | 95 | |
| Phe | Phe | His | Arg | Leu | Glu | Glu | Ser | Phe | Leu | Val | Glu | Glu | Asp | Lys | Lys |
| | | | 100 | | | | | 105 | | | | | 110 | | |
| His | Glu | Arg | His | Pro | Ile | Phe | Gly | Asn | Ile | Val | Asp | Glu | Val | Ala | Tyr |
| | | | 115 | | | | | 120 | | | | | 125 | | |
| His | Glu | Lys | Tyr | Pro | Thr | Ile | Tyr | His | Leu | Arg | Lys | Lys | Leu | Val | Asp |
| | | | 130 | | | | | 135 | | | | | 140 | | |
| Ser | Thr | Asp | Lys | Ala | Asp | Leu | Arg | Leu | Ile | Tyr | Leu | Ala | Leu | Ala | His |
| 145 | | | | | 150 | | | | | 155 | | | | | 160 |
| Met | Ile | Lys | Phe | Arg | Gly | His | Phe | Leu | Ile | Glu | Gly | Asp | Leu | Asn | Pro |
| | | | | 165 | | | | | 170 | | | | | 175 | |
| Asp | Asn | Ser | Asp | Val | Asp | Lys | Leu | Phe | Ile | Gln | Leu | Val | Gln | Thr | Tyr |
| | | | 180 | | | | | 185 | | | | | 190 | | |
| Asn | Gln | Leu | Phe | Glu | Glu | Asn | Pro | Ile | Asn | Ala | Ser | Gly | Val | Asp | Ala |
| | | | 195 | | | | | 200 | | | | | 205 | | |
| Lys | Ala | Ile | Leu | Ser | Ala | Arg | Leu | Ser | Lys | Ser | Arg | Arg | Leu | Glu | Asn |
| | 210 | | | | | 215 | | | | | 220 | | | | |
| Leu | Ile | Ala | Gln | Leu | Pro | Gly | Glu | Lys | Lys | Asn | Gly | Leu | Phe | Gly | Asn |
| 225 | | | | | 230 | | | | | 235 | | | | | 240 |
| Leu | Ile | Ala | Leu | Ser | Leu | Gly | Leu | Thr | Pro | Asn | Phe | Lys | Ser | Asn | Phe |
| | | | | 245 | | | | | 250 | | | | | 255 | |
| Asp | Leu | Ala | Glu | Asp | Ala | Lys | Leu | Gln | Leu | Ser | Lys | Asp | Thr | Tyr | Asp |
| | | | 260 | | | | | 265 | | | | | 270 | | |
| Asp | Asp | Leu | Asp | Asn | Leu | Leu | Ala | Gln | Ile | Gly | Asp | Gln | Tyr | Ala | Asp |
| | | | 275 | | | | | 280 | | | | | 285 | | |
| Leu | Phe | Leu | Ala | Ala | Lys | Asn | Leu | Ser | Asp | Ala | Ile | Leu | Leu | Ser | Asp |
| | 290 | | | | | 295 | | | | | 300 | | | | |
| Ile | Leu | Arg | Val | Asn | Thr | Glu | Ile | Thr | Lys | Ala | Pro | Leu | Ser | Ala | Ser |
| 305 | | | | | 310 | | | | | 315 | | | | | 320 |
| Met | Ile | Lys | Arg | Tyr | Asp | Glu | His | His | Gln | Asp | Leu | Thr | Leu | Leu | Lys |
| | | | | 325 | | | | | 330 | | | | | 335 | |
| Ala | Leu | Val | Arg | Gln | Gln | Leu | Pro | Glu | Lys | Tyr | Lys | Glu | Ile | Phe | Phe |
| | | | 340 | | | | | 345 | | | | | 350 | | |
| Asp | Gln | Ser | Lys | Asn | Gly | Tyr | Ala | Gly | Tyr | Ile | Asp | Gly | Gly | Ala | Ser |
| | | | 355 | | | | | 360 | | | | | 365 | | |
| Gln | Glu | Glu | Phe | Tyr | Lys | Phe | Ile | Lys | Pro | Ile | Leu | Glu | Lys | Met | Asp |
| | | | 370 | | | | | 375 | | | | | 380 | | |

-continued

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu

-continued

```
                    805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
                850                 855                 860
Gly Lys Ser Asp Asn Val Pro Ser Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
1010                1015                1020
Lys Ser Glu Gln Glu Ile Gly Lys Ala Thr Ala Lys Tyr Phe Phe
1025                1030                1035
Tyr Ser Asn Ile Met Asn Phe Phe Lys Thr Glu Ile Thr Leu Ala
1040                1045                1050
Asn Gly Glu Ile Arg Lys Arg Pro Leu Ile Glu Thr Asn Gly Glu
1055                1060                1065
Thr Gly Glu Ile Val Trp Asp Lys Gly Arg Asp Phe Ala Thr Val
1070                1075                1080
Arg Lys Val Leu Ser Met Pro Gln Val Asn Ile Val Lys Lys Thr
1085                1090                1095
Glu Val Gln Thr Gly Gly Phe Ser Lys Glu Ser Ile Leu Pro Lys
1100                1105                1110
Arg Asn Ser Asp Lys Leu Ile Ala Arg Lys Lys Asp Trp Asp Pro
1115                1120                1125
Lys Lys Tyr Gly Gly Phe Asp Ser Pro Thr Val Ala Tyr Ser Val
1130                1135                1140
Leu Val Val Ala Lys Val Glu Lys Gly Lys Ser Lys Lys Leu Lys
1145                1150                1155
Ser Val Lys Glu Leu Leu Gly Ile Thr Ile Met Glu Arg Ser Ser
1160                1165                1170
Phe Glu Lys Asn Pro Ile Asp Phe Leu Glu Ala Lys Gly Tyr Lys
1175                1180                1185
Glu Val Lys Lys Asp Leu Ile Ile Lys Leu Pro Lys Tyr Ser Leu
1190                1195                1200
Phe Glu Leu Glu Asn Gly Arg Lys Arg Met Leu Ala Ser Ala Gly
1205                1210                1215
```

```
Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
1235            1240            1245

Pro Glu Asp Asn Glu Gln Lys Gln Leu Phe Val Glu Gln His Lys
1250            1255            1260

His Tyr Leu Asp Glu Ile Ile Glu Gln Ile Ser Glu Phe Ser Lys
1265            1270            1275

Arg Val Ile Leu Ala Asp Ala Asn Leu Asp Lys Val Leu Ser Ala
1280            1285            1290

Tyr Asn Lys His Arg Asp Lys Pro Ile Arg Glu Gln Ala Glu Asn
1295            1300            1305

Ile Ile His Leu Phe Thr Leu Thr Asn Leu Gly Ala Pro Ala Ala
1310            1315            1320

Phe Lys Tyr Phe Asp Thr Thr Ile Asp Arg Lys Arg Tyr Thr Ser
1325            1330            1335

Thr Lys Glu Val Leu Asp Ala Thr Leu Ile His Gln Ser Ile Thr
1340            1345            1350

Gly Leu Tyr Glu Thr Arg Ile Asp Leu Ser Gln Leu Gly Gly Asp
1355            1360            1365

<210> SEQ ID NO 6
<211> LENGTH: 20
<212> TYPE: DNA
<213> ORGANISM: Artificial
<220> FEATURE:
<223> OTHER INFORMATION: spacer sequence_fourth base from the PAM end
      space is mutated to an adenine
<220> FEATURE:
<221> NAME/KEY: misc_feature
<222> LOCATION: (1)..(20)
<223> OTHER INFORMATION: n is a, c, g, or t

<400> SEQUENCE: 6
nnnnnnnnnn nnnnnnnnnn                                           20

<210> SEQ ID NO 7
<211> LENGTH: 30
<212> TYPE: DNA
<213> ORGANISM: Artificial
<220> FEATURE:
<223> OTHER INFORMATION: GFP control spacer

<400> SEQUENCE: 7
actacaagac acgtgctgaa gtcaagtttg                                30

<210> SEQ ID NO 8
<211> LENGTH: 35
<212> TYPE: DNA
<213> ORGANISM: Artificial
<220> FEATURE:
<223> OTHER INFORMATION: GFP control insert

<400> SEQUENCE: 8
ggttactaca agacacgtgc tgaagtcaag tttgg                          35

<210> SEQ ID NO 9
<211> LENGTH: 35
<212> TYPE: DNA
<213> ORGANISM: Artificial
<220> FEATURE:
<223> OTHER INFORMATION: GFP control insert
```

<400> SEQUENCE: 9 aaaccaaaact tgacttcagc acgtgtcttg tagta                                      35

<210> SEQ ID NO 10
<211> LENGTH: 70
<212> TYPE: DNA
<213> ORGANISM: Artificial
<220> FEATURE:
<223> OTHER INFORMATION: heteroduplex

<400> SEQUENCE: 10
ggttactaca agacacgtgc tgaagtcaag tttggatgat gttctgtgca cgacttcagt           60
tcaaaccaaa                                                                  70

<210> SEQ ID NO 11
<211> LENGTH: 60
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (29)..(32)
<223> OTHER INFORMATION: n is a, c, g, or t

<400> SEQUENCE: 11
ctttccctac acgacgctct tccgatctnn nngtagagat tgacatccct atcagtgata           60

<210> SEQ ID NO 12
<211> LENGTH: 55
<212> TYPE: DNA
<213> ORGANISM: Artificial
<220> FEATURE:
<223> OTHER INFORMATION: primer

<400> SEQUENCE: 12
ggagttcaga cgtgtgctct tccgatctag acgttcccgt tgaatatggc tcata               55

<210> SEQ ID NO 13
<211> LENGTH: 30
<212> TYPE: DNA
<213> ORGANISM: Artificial
<220> FEATURE:
<223> OTHER INFORMATION: spacer

<400> SEQUENCE: 13
acatagcaga actttaaaag tgctcatcaa                                            30

<210> SEQ ID NO 14
<211> LENGTH: 30
<212> TYPE: DNA
<213> ORGANISM: Artificial
<220> FEATURE:
<223> OTHER INFORMATION: spacer

<400> SEQUENCE: 14
acatagcaga actttaaaag tgctcatcag                                            30

<210> SEQ ID NO 15
<211> LENGTH: 30
<212> TYPE: DNA
<213> ORGANISM: Artificial
<220> FEATURE:
<223> OTHER INFORMATION: spacer

```
<400> SEQUENCE: 15
acatagcaga actttaaaag tgctcatcac                                    30

<210> SEQ ID NO 16
<211> LENGTH: 30
<212> TYPE: DNA
<213> ORGANISM: Artificial
<220> FEATURE:
<223> OTHER INFORMATION: spacer

<400> SEQUENCE: 16
acatagcaga actttaaaag tgctcatctt                                    30

<210> SEQ ID NO 17
<211> LENGTH: 30
<212> TYPE: DNA
<213> ORGANISM: Artificial
<220> FEATURE:
<223> OTHER INFORMATION: spacer

<400> SEQUENCE: 17
acatagcaga actttaaaag tgctcatcgt                                    30

<210> SEQ ID NO 18
<211> LENGTH: 30
<212> TYPE: DNA
<213> ORGANISM: Artificial
<220> FEATURE:
<223> OTHER INFORMATION: spacer

<400> SEQUENCE: 18
acatagcaga actttaaaag tgctcatcct                                    30

<210> SEQ ID NO 19
<211> LENGTH: 30
<212> TYPE: DNA
<213> ORGANISM: Artificial
<220> FEATURE:
<223> OTHER INFORMATION: spacer

<400> SEQUENCE: 19
acatagcaga actttaaaag tgctcataat                                    30

<210> SEQ ID NO 20
<211> LENGTH: 30
<212> TYPE: DNA
<213> ORGANISM: Artificial
<220> FEATURE:
<223> OTHER INFORMATION: spacer

<400> SEQUENCE: 20
acatagcaga actttaaaag tgctcattat                                    30

<210> SEQ ID NO 21
<211> LENGTH: 30
<212> TYPE: DNA
<213> ORGANISM: Artificial
<220> FEATURE:
<223> OTHER INFORMATION: spacer

<400> SEQUENCE: 21
acatagcaga actttaaaag tgctcatgat                                    30

<210> SEQ ID NO 22
<211> LENGTH: 30
```

```
<212> TYPE: DNA
<213> ORGANISM: Artificial
<220> FEATURE:
<223> OTHER INFORMATION: spacer

<400> SEQUENCE: 22
acatagcaga actttaaaag tgctcaacat                                           30

<210> SEQ ID NO 23
<211> LENGTH: 30
<212> TYPE: DNA
<213> ORGANISM: Artificial
<220> FEATURE:
<223> OTHER INFORMATION: spacer

<400> SEQUENCE: 23
acatagcaga actttaaaag tgctcagcat                                           30

<210> SEQ ID NO 24
<211> LENGTH: 30
<212> TYPE: DNA
<213> ORGANISM: Artificial
<220> FEATURE:
<223> OTHER INFORMATION: spacer

<400> SEQUENCE: 24
acatagcaga actttaaaag tgctcaccat                                           30

<210> SEQ ID NO 25
<211> LENGTH: 30
<212> TYPE: DNA
<213> ORGANISM: Artificial
<220> FEATURE:
<223> OTHER INFORMATION: spacer

<400> SEQUENCE: 25
acatagcaga actttaaaag tgctcttcat                                           30

<210> SEQ ID NO 26
<211> LENGTH: 30
<212> TYPE: DNA
<213> ORGANISM: Artificial
<220> FEATURE:
<223> OTHER INFORMATION: spacer

<400> SEQUENCE: 26
acatagcaga actttaaaag tgctcgtcat                                           30

<210> SEQ ID NO 27
<211> LENGTH: 30
<212> TYPE: DNA
<213> ORGANISM: Artificial
<220> FEATURE:
<223> OTHER INFORMATION: spacer

<400> SEQUENCE: 27
acatagcaga actttaaaag tgctcctcat                                           30

<210> SEQ ID NO 28
<211> LENGTH: 30
<212> TYPE: DNA
<213> ORGANISM: Artificial
<220> FEATURE:
<223> OTHER INFORMATION: spacer

<400> SEQUENCE: 28
```
acatagcaga actttaaaag tgctaatcat                                    30

<210> SEQ ID NO 29
<211> LENGTH: 30
<212> TYPE: DNA
<213> ORGANISM: Artificial
<220> FEATURE:
<223> OTHER INFORMATION: spacer

<400> SEQUENCE: 29
acatagcaga actttaaaag tgcttatcat                                    30

<210> SEQ ID NO 30
<211> LENGTH: 30
<212> TYPE: DNA
<213> ORGANISM: Artificial
<220> FEATURE:
<223> OTHER INFORMATION: spacer

<400> SEQUENCE: 30
acatagcaga actttaaaag tgctgatcat                                    30

<210> SEQ ID NO 31
<211> LENGTH: 30
<212> TYPE: DNA
<213> ORGANISM: Artificial
<220> FEATURE:
<223> OTHER INFORMATION: spacer

<400> SEQUENCE: 31
acatagcaga actttaaaag tgcacatcat                                    30

<210> SEQ ID NO 32
<211> LENGTH: 30
<212> TYPE: DNA
<213> ORGANISM: Artificial
<220> FEATURE:
<223> OTHER INFORMATION: spacer

<400> SEQUENCE: 32
acatagcaga actttaaaag tgcgcatcat                                    30

<210> SEQ ID NO 33
<211> LENGTH: 30
<212> TYPE: DNA
<213> ORGANISM: Artificial
<220> FEATURE:
<223> OTHER INFORMATION: spacer

<400> SEQUENCE: 33
acatagcaga actttaaaag tgcccatcat                                    30

<210> SEQ ID NO 34
<211> LENGTH: 30
<212> TYPE: DNA
<213> ORGANISM: Artificial
<220> FEATURE:
<223> OTHER INFORMATION: spacer

<400> SEQUENCE: 34
acatagcaga actttaaaag tactcatcat                                    30

<210> SEQ ID NO 35
<211> LENGTH: 30
<212> TYPE: DNA
<213> ORGANISM: Artificial

```
<220> FEATURE:
<223> OTHER INFORMATION: spacer

<400> SEQUENCE: 35
acatagcaga actttaaaag ttctcatcat                                              30

<210> SEQ ID NO 36
<211> LENGTH: 30
<212> TYPE: DNA
<213> ORGANISM: Artificial
<220> FEATURE:
<223> OTHER INFORMATION: spacer

<400> SEQUENCE: 36
acatagcaga actttaaaag tcctcatcat                                              30

<210> SEQ ID NO 37
<211> LENGTH: 30
<212> TYPE: DNA
<213> ORGANISM: Artificial
<220> FEATURE:
<223> OTHER INFORMATION: spacer

<400> SEQUENCE: 37
acatagcaga actttaaaag agctcatcat                                              30

<210> SEQ ID NO 38
<211> LENGTH: 30
<212> TYPE: DNA
<213> ORGANISM: Artificial
<220> FEATURE:
<223> OTHER INFORMATION: spacer

<400> SEQUENCE: 38
acatagcaga actttaaaag ggctcatcat                                              30

<210> SEQ ID NO 39
<211> LENGTH: 30
<212> TYPE: DNA
<213> ORGANISM: Artificial
<220> FEATURE:
<223> OTHER INFORMATION: spacer

<400> SEQUENCE: 39
acatagcaga actttaaaag cgctcatcat                                              30

<210> SEQ ID NO 40
<211> LENGTH: 30
<212> TYPE: DNA
<213> ORGANISM: Artificial
<220> FEATURE:
<223> OTHER INFORMATION: spacer

<400> SEQUENCE: 40
acatagcaga actttaaaag tgctcatcat                                              30

<210> SEQ ID NO 41
<211> LENGTH: 30
<212> TYPE: DNA
<213> ORGANISM: Artificial
<220> FEATURE:
<223> OTHER INFORMATION: spacer

<400> SEQUENCE: 41
actacaagac acgtgctgaa gtcaagtttg                                              30
```

```
<210> SEQ ID NO 42
<211> LENGTH: 30
<212> TYPE: DNA
<213> ORGANISM: Artificial
<220> FEATURE:
<223> OTHER INFORMATION: NGA PAM

<400> SEQUENCE: 42
gggttgttct ggtccataaa ctgaggaagc                                    30

<210> SEQ ID NO 43
<211> LENGTH: 30
<212> TYPE: DNA
<213> ORGANISM: Artificial
<220> FEATURE:
<223> OTHER INFORMATION: PAM

<400> SEQUENCE: 43
gttccagcca gctgtctcag tttatgaacc                                    30

<210> SEQ ID NO 44
<211> LENGTH: 30
<212> TYPE: DNA
<213> ORGANISM: Artificial
<220> FEATURE:
<223> OTHER INFORMATION: SEQ ID NO:45

<400> SEQUENCE: 44
cttcggttcc agccagctgt ctcagtttat                                    30

<210> SEQ ID NO 45
<211> LENGTH: 30
<212> TYPE: DNA
<213> ORGANISM: Artificial
<220> FEATURE:
<223> OTHER INFORMATION: PAM

<400> SEQUENCE: 45
tcgccccgaa gaacgttttc caatggtgag                                    30

<210> SEQ ID NO 46
<211> LENGTH: 30
<212> TYPE: DNA
<213> ORGANISM: Artificial
<220> FEATURE:
<223> OTHER INFORMATION: PAM

<400> SEQUENCE: 46
ccccgaagaa cgttttccaa tgatgagtac                                    30

<210> SEQ ID NO 47
<211> LENGTH: 30
<212> TYPE: DNA
<213> ORGANISM: Artificial
<220> FEATURE:
<223> OTHER INFORMATION: PAM

<400> SEQUENCE: 47
actacaagac acgtgctgaa gtcaagtttg                                    30
```